US012622738B2

(12) United States Patent
Foster et al.

(10) Patent No.: US 12,622,738 B2
(45) Date of Patent: May 12, 2026

(54) MEDICAL DEVICES AND RELATED METHODS

(71) Applicant: Boston Scientific Scimed Inc., Maple Grove, MN (US)

(72) Inventors: Daniel J. Foster, Lino Lakes, MN (US); Matthew P. Jones, Shoreview, MN (US); Allyn N. Jensrud, Brookline, MA (US); John Kummailil, Sherborn, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 426 days.

(21) Appl. No.: 17/339,097

(22) Filed: Jun. 4, 2021

(65) Prior Publication Data

US 2021/0386472 A1     Dec. 16, 2021

Related U.S. Application Data

(60) Provisional application No. 63/037,185, filed on Jun. 10, 2020.

(51) Int. Cl.
*A61B 18/14*          (2006.01)
*A61B 18/00*          (2006.01)

(52) U.S. Cl.
CPC .... *A61B 18/14* (2013.01); *A61B 2018/00077* (2013.01); *A61B 2018/00083* (2013.01); *A61B 2218/002* (2013.01)

(58) Field of Classification Search
CPC .......... A61B 18/14; A61B 2018/00077; A61B 2018/00083; A61B 2218/002;

(Continued)

(56) References Cited

U.S. PATENT DOCUMENTS 4,202,337 A * 5/1980 Hren ................. A61B 18/1402
606/50
5,697,926 A * 12/1997 Weaver ............. A61B 18/1402
606/41

(Continued)

FOREIGN PATENT DOCUMENTS

CN      102307522 A      1/2012
DE      4035267 A1      5/1991

(Continued)

OTHER PUBLICATIONS

Fotovvati et al., "On Coating Techniques for Surface Protection: A Review", Journal of Manufacturing and Materials Processing, Mar. 25, 2019 (22 pages).

(Continued)

*Primary Examiner* — Ronald Hupczey, Jr.
*Assistant Examiner* — Ana Veruska Guerrero
(74) *Attorney, Agent, or Firm* — Bookoff McAndrews PLLC

(57) ABSTRACT

A medical device includes an electrode shaft and a tip. The electrode shaft is configured to deliver energy to a target site and includes an electrode shaft lumen configured to deliver fluid to the target site. The tip is coupled to a distal tip of the electrode shaft. The tip includes an inner portion of conductive material and an exterior layer of insulative material. The tip includes a tip lumen fluidly connected to the electrode shaft lumen and configured to deliver fluid to the target site.

19 Claims, 12 Drawing Sheets

(58) Field of Classification Search
CPC  A61B 2018/00327; A61B 2018/00482; A61B
2018/00559; A61B 2018/1417; A61B
18/1482; A61B 18/1485; A61B 18/1492;
A61B 18/148; A61B 2018/046; A61B
2018/00011; A61B 2018/0072; A61B
2018/00767; A61B 2018/00779
See application file for complete search history.

(56)                References Cited

U.S. PATENT DOCUMENTS

| | | | | |
|---|---|---|---|---|
| 5,807,395 A * | 9/1998 | Mulier | ............... | A61B 18/1477 606/41 |
| 5,902,272 A * | 5/1999 | Eggers | ................... | A61B 18/12 604/114 |
| 7,211,063 B2 * | 5/2007 | Tom | ..................... | A61B 5/6885 606/108 |
| 7,211,067 B2 * | 5/2007 | Hawk | ................ | A61B 17/3478 604/164.01 |
| 7,231,260 B2 * | 6/2007 | Wallace | ................. | A61N 1/057 607/116 |
| 7,244,242 B2 * | 7/2007 | Freyman | ........... | A61M 25/1002 604/96.01 |
| 7,270,654 B2 * | 9/2007 | Griego | .............. | A61M 25/0026 604/82 |
| 7,282,051 B2 * | 10/2007 | Rioux | ................ | A61B 18/1477 606/41 |
| 7,347,859 B2 * | 3/2008 | Garabedian | .......... | A61B 18/148 606/41 |
| 7,371,236 B2 * | 5/2008 | Okada | ................ | A61B 18/1402 606/45 |
| 7,493,160 B2 * | 2/2009 | Weber | ................... | A61M 25/00 607/3 |
| 7,632,266 B2 * | 12/2009 | Scopton | ............. | A61B 18/1482 606/49 |
| 8,425,510 B2 * | 4/2013 | Yamamoto | ......... | A61B 18/1492 606/41 |
| 9,597,463 B2 * | 3/2017 | Li | ..................... | A61M 25/0084 |
| 2009/0254085 A1 * | 10/2009 | Yamamoto | ............. | A61B 1/018 606/46 |
| 2012/0157991 A1 * | 6/2012 | Christian | ........... | A61B 18/1492 606/41 |
| 2013/0226176 A1 | 8/2013 | Kuehner et al. | | |
| 2014/0288554 A1 * | 9/2014 | Okada | ................ | A61B 18/1492 606/45 |
| 2016/0220301 A1 * | 8/2016 | Yamamoto | ............. | A61B 18/14 |
| 2019/0298435 A1 * | 10/2019 | Estevez | .................. | A61B 18/14 |
| 2020/0060756 A1 * | 2/2020 | Smith | .................. | A61B 18/148 |

FOREIGN PATENT DOCUMENTS

| | | | | |
|---|---|---|---|---|
| EP | 1 715 910 A1 | 11/2006 | | |
| WO | WO-9321845 A1 * | 11/1993 | ......... | A61B 18/1233 |
| WO | WO-2005079901 A1 * | 9/2005 | ....... | A61B 7/320016 |
| WO | WO-2014042039 A1 * | 3/2014 | ............. | A61B 18/14 |
| WO | WO-2018013354 A1 * | 1/2018 | ......... | A61B 17/2909 |

OTHER PUBLICATIONS

International Search Report and Written Opinion issued in International Application No. PCT/US2021/035878, issued Oct. 1, 2021 (13 pages).

* cited by examiner

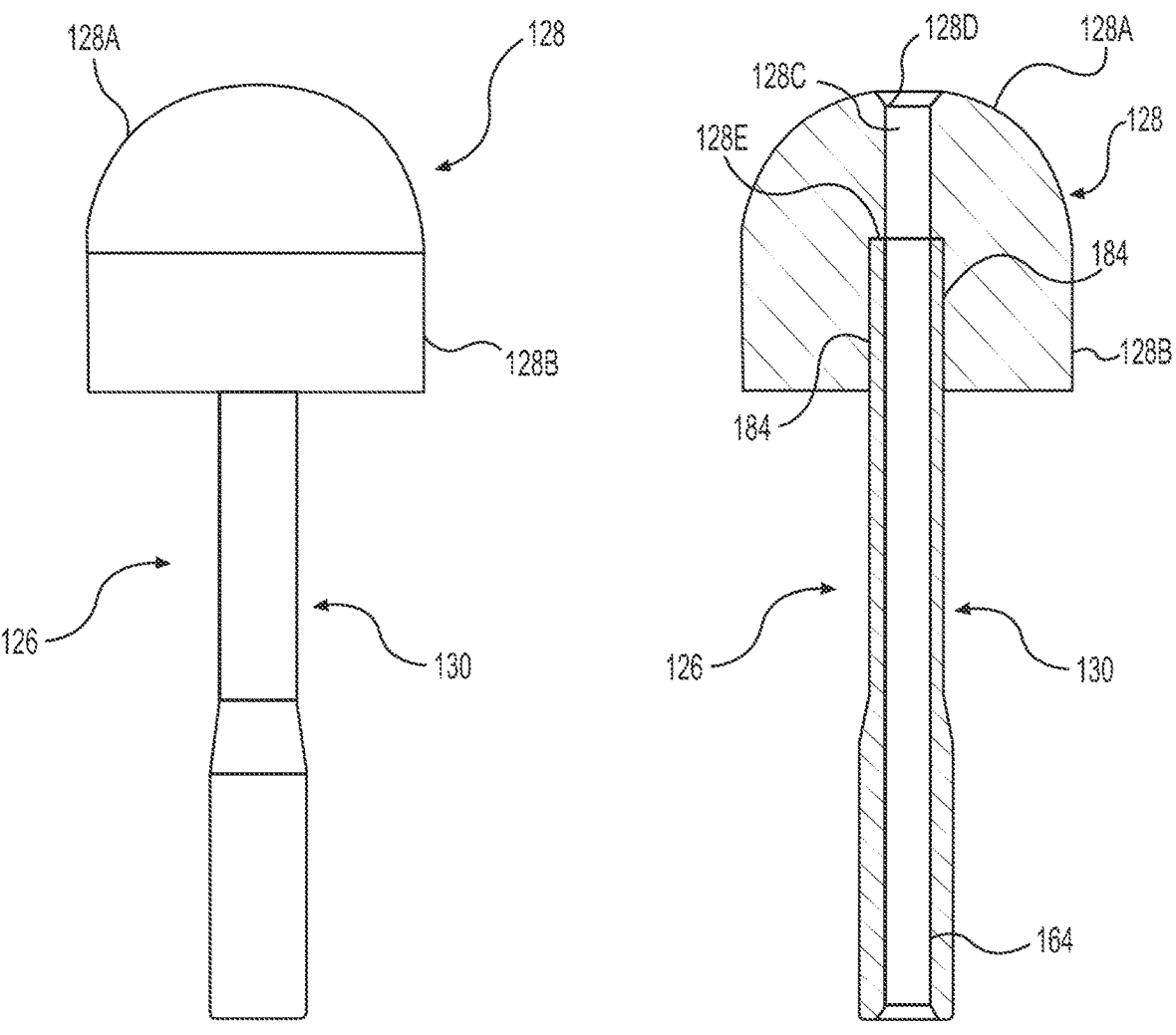
FIG. 3A          FIG. 3B

MEDICAL DEVICES AND RELATED METHODS

CROSS-REFERENCE TO RELATED APPLICATIONS

This present disclosure claims priority to U.S. Provisional Patent Application No. 63/037,185, filed on Jun. 10, 2020, the disclosure of which is incorporated herewith by reference.

TECHNICAL FIELD

Aspects of this disclosure generally relate to medical devices and related methods. Embodiments of the disclosure relate to medical devices and related methods configured for the treatment of tissue by delivering electrical energy to or into tissue and/or injecting fluid into and/or under tissue with an electrode having an insulated distal tip.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle and an energy delivery device for purposes of raising, separating, flushing, cutting, dissecting, ablating, marking, coagulating, cauterizing, or otherwise treating and/or manipulating tissue. The injection and energy delivery may be performed separately. For example, in order to deliver energy to the tissue, the user may be required to remove the injection needle from the insertion device and deliver the energy delivery device through the insertion device to the tissue being targeted, and vice versa. During the procedure, the user may alternate using the injection needle and the energy delivery device, and exchanging devices may increase the duration and risks of the medical procedure. Additionally, one or more portions of the energy delivery device may inadvertently contact or harm tissue (or an inner channel of the insertion device) when energized.

The devices and methods of this disclosure may rectify one or more of the deficiencies described above or address other aspects of the art.

SUMMARY

Examples of the disclosure relate to, among other things, medical devices configured for treating tissue by delivering electrical energy to the tissue, and configured for delivering fluid into and/or under the tissue. Each of the examples disclosed herein may include one or more of the features described in connection with any of the other disclosed examples.

In one example, a medical device may include an electrode shaft and a tip. The electrode shaft may be configured to deliver energy to a target site and may include an electrode shaft lumen configured to deliver fluid to the target site. The tip may be coupled to a distal tip of the electrode shaft. The tip may include an inner portion of conductive material and an exterior layer of insulative material. The tip may include a tip lumen fluidly connected to the electrode shaft lumen and configured to deliver fluid to the target site.

The medical device may include one or more of the following features. An entire exterior of the tip may include the exterior layer. The exterior layer may be formed by a sputtering procedure. The insulative material may be ceramic. The exterior layer may be approximately 300 microns thick. The tip may include a rounded distal end and a cylindrical side portion. The tip may be cylindrical. The tip may include rounded edges.

The medical device may further include an electrode plate on a proximal end of the tip. The electrode plate may be conductive and may be electrically connected to the electrode shaft such that the electrode plate is energized when the electrode shaft is energized. The electrode plate may be circular and may cover an entirety of the proximal end of the tip. The electrode plate may be triangular or star-shaped.

The electrode shaft may include a plurality of insulated portions, and the insulated portions may be longitudinally spaced apart on a length of the electrode shaft. The electrode shaft and the inner portion of the tip may be formed of a metallic material, and the electrode shaft and the tip may be welded together. The electrode shaft and the inner portion of the tip may be formed of one piece of metallic material.

In another example, a medical device may include a handle, a shaft, a conductive element, and an electrode. The handle may include a fluid port and an energy receiving hub. The shaft may include a shaft lumen configured to direct a flow of fluid through the shaft from the fluid port. The conductive element may be electrically connected to the energy receiving hub and may pass through at least a portion of the handle and/or the shaft. The electrode may be coupled to a distal end of the shaft. The electrode may include an electrode shaft and a tip extending distally from the electrode shaft. The tip may include an inner portion of conductive material and an exterior layer of an insulative material. The electrode shaft may be electrically connected to the conductive element and includes an electrode shaft lumen fluidly connected to the shaft lumen. The tip may include a tip lumen fluidly connected to the electrode shaft lumen and configured to deliver fluid from a distal end of the electrode.

The medical device may include one or more of the following features. The handle may further include a main body and a movable body. Movement of the movable body relative to the main body may move the electrode relative to the distal end of the shaft. With the movable body in a proximally retracted position, only the tip may be exposed distally beyond the shaft. With the movable body in a distally extended position, the tip and at least a portion of the electrode shaft may be exposed distally beyond the shaft.

In yet another example, a medical device may include an electrode shaft and a tip. The electrode shaft may include an electrode shaft lumen configured to receive fluid. The tip may be coupled to a distal tip of the electrode shaft and may include an inner portion of conductive material and an exterior layer of insulative material. The exterior layer may insulate at least a distal portion of the medical device. The tip may include a tip lumen fluidly connected to the electrode shaft lumen to form a channel. The channel may extend along a longitudinal axis of the medical device.

The medical device may include one or more of the following features. The tip may include a rounded distal portion and a cylindrical side portion. An entire exterior of the tip may comprise the exterior layer. The insulative material may be ceramic. The exterior layer may be approximately 300 microns thick.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 3A illustrates a side view of an alternative exemplary electrode portion of the medical device of FIGS. 1A and 1B, and FIG. 3B illustrates a cross-sectional view of the electrode portion of FIG. 3A, according to aspects of the disclosure.

DETAILED DESCRIPTION

Examples of the disclosure include devices and methods for: facilitating and improving the efficacy, efficiency, and safety of treating and/or manipulating tissue when, for example, applying electrical energy to tissue with an electrode; delivering fluid into and/or under tissue during a medical procedure through the distal end of the electrode; and insulating a distal tip of the electrode. For example, aspects of the disclosure may provide a user (e.g., physician, medical technician, or other medical service provider) with the ability to apply electrical energy or heat to tissue using a medical device having an electrode, and to deliver fluid into and/or under tissue with the same medical device. Aspects of the disclosure may provide the user with the ability to apply electrical energy or heat and deliver fluid with a reduced likelihood of damaging tissue or contacting unintended portions of the tissue. Aspects of the disclosure may help the user penetrate a layer of tissue (e.g., a submucosal layer) to cause perforation. In these aspects, an insulated portion of the device may help maintain a separation between a cutting portion of the device. Furthermore, aspects of the disclosure include steps to manufacture or otherwise form one or more electrodes and/or distal tips of a medical device. Some aspects of the disclosure may be used in performing an endoscopic, laparoscopic, arthroscopic, gynoscopic, thoracoscopic, cystoscopic, or other type of procedure.

Reference will now be made in detail to examples of the disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figures 1A, 1B:
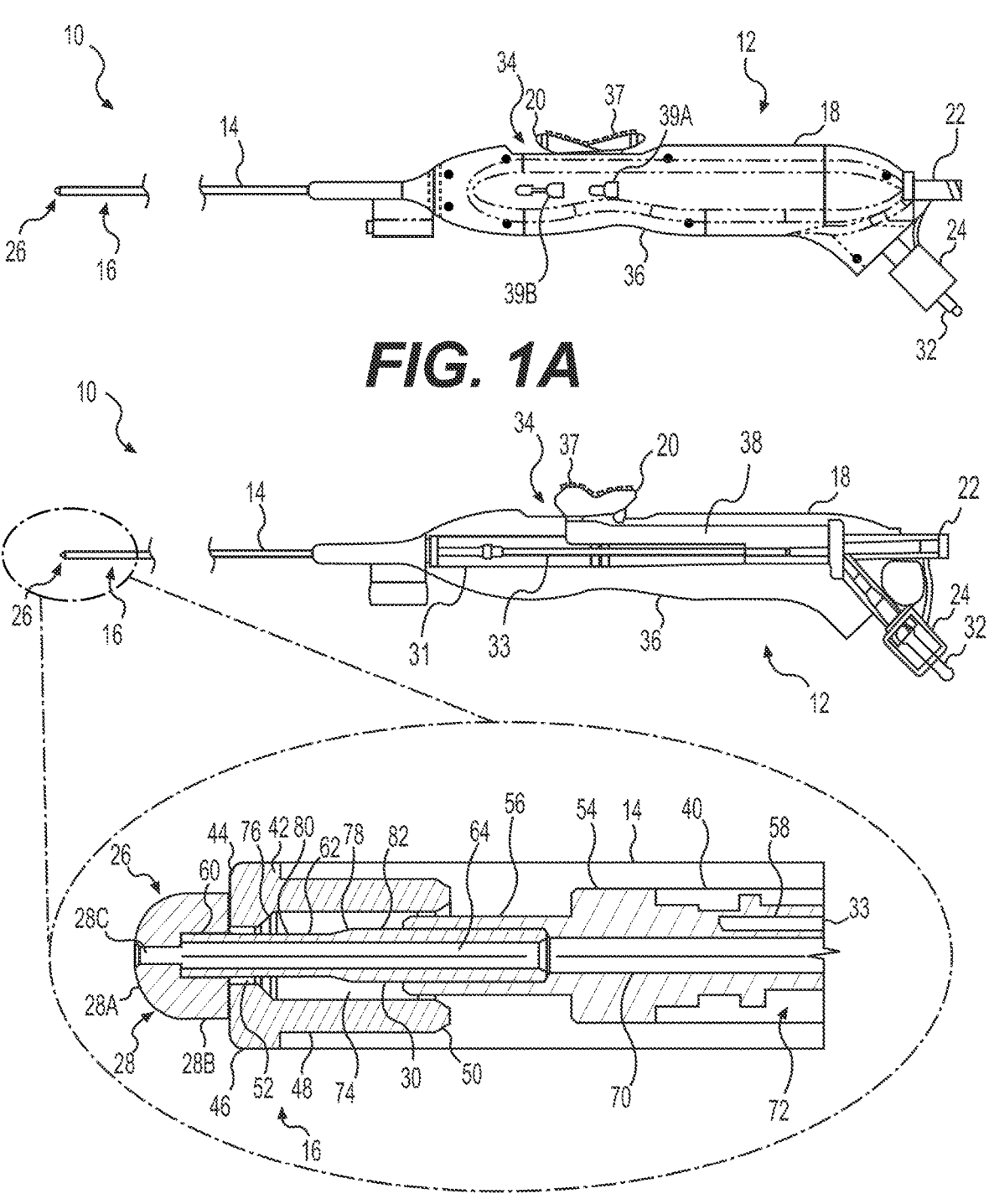
FIG. 1A illustrates an exemplary medical device.
FIG. 1B illustrates a cross-sectional view of the medical device with a distal portion of the medical device enlarged, according to aspects of this disclosure.

FIGS. 1A and 1B depict a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an end effector, for example, an electrode portion 26 (hereinafter "electrode 26"). Electrode 26 is electrically connected to hub 24, and as discussed in detail below, may include a channel fluidly connected to, or otherwise in fluid communication with, port 22. Additionally, as shown in FIG. 1B and discussed in detail below, electrode 26 may include an insulation tip 28, which may at least partially surround a distal portion of an electrode shaft 30.

Medical device 10 may be inserted into a body lumen of a subject, either through an insertion device (not shown) or alone, such that at least a portion of shaft 14 may be within the subject, while handle 12 may remain outside of the subject. Distal end 16 may be positioned at a target site within the subject. From outside of the subject, a user can manipulate handle 12. Movement of movable body 20 relative to main body 18 in a first direction (e.g., the distal direction) may extend electrode 26 relative to shaft 14 (e.g., move electrode 26 distally relative to a distal end of shaft 14), while movement of movable body 20 relative to main body 18 in a second direction (e.g., the proximal direction) may retract electrode 26 relative to shaft 14 (e.g., move electrode 26 proximally relative to a distal end of shaft 14). Although not shown, movable body 20 or additional components of handle 12 may articulate electrode 26 (or electrode 26 and distal end 16) left or right, and/or up or down relative to shaft 14.

Handle 12 may be coupled to a fluid source (not shown) via port 22. Port 22 may be in fluid communication with electrode 26 via an internal lumen 31, which may extend through handle 12 (FIG. 1B) and shaft 14. It is noted that various portions of handle 12 shown in FIG. 1B may not be to scale, in order to more fully illustrate various portions of handle 12. In one aspect, internal lumen 31 may extend longitudinally through main body 18 of handle 12 and shaft 14 to fluidly connect port 22 to electrode 26. Port 22 may be positioned on a proximal portion of main body 18, for example, a proximal end of main body 18. Alternatively, port 22 may be positioned on a distal or central portion of main body 18. Moreover, port 22 may include a one-way valve, a luer, a seal, threading, and/or any appropriate element to help maintain a secure connection between handle 12 and the fluid source, minimize or prevent back-flow (e.g., fluid flowing proximally out of port 22), and/or minimize or prevent leakage. In one example, a one-way valve may include an outer housing containing an inner elastomeric and/or gelatinous sealing member (not shown).

Handle 12 may be coupled to an energy source (not shown) through hub 24. Hub 24 may include one or more prongs or pins 32 to couple to the energy source. Hub 24 may be electrically coupled to electrode 26 via a conductive element 33, which may be electrically coupled to pin 32 and extend through handle 12 and through at least a portion of shaft 14. The energy source may be an electrocautery source, a radio frequency generator, a heating source, a current generator, etc. In one aspect, medical device 10 may be used for monopolar electrosurgery, and may include a return electrode positioned remotely from electrode 26 on or otherwise adjacent the subject. In another aspect, medical device 10 may be used for bipolar electrosurgery. In that instance, electrode 26 may include an active electrode portion, and a return electrode may be provided at or near another portion of electrode 26 and/or shaft 14. In one example, although not shown, two conductive elements may run through shaft 14, where the conductive elements may be electrically isolated from each other, allowing one to conduct energy to the active electrode and the other to conduct energy from a return electrode.

Hub 24 may be positioned on main body 18, for example, on a proximal end of main body 18. In one aspect, port 22 may extend from the proximal end of main body 18 in a direction parallel to a longitudinal axis of main body 18, and hub 24 may extend from the proximal end of main body 18 at an angle transverse (e.g., approximately 45 degrees) to the longitudinal axis of main body 18. In another aspect, hub 24 may be positioned on a distal or central portion of main body 18, or on movable body 20. Although not shown, main body 18 and/or hub 24 may include a one-way valve, a luer, a seal, threading, and/or any appropriate element to help maintain a secure connection between handle 12 and the energy source, minimize or prevent back-flow (e.g., fluid flowing from port 22 and/or internal lumen 31 and proximally out of hub 24), and/or minimize or prevent leakage.

In one aspect shown in FIG. 1B, pin 32 may extend through hub 24 transverse to a longitudinal axis of handle 12, and may be electrically and physically connected to conductive element 33, such as a wire, a cable, and/or a braided sheath. Conductive element 33 may be electrically conductive or include an electrically conductive element, and conductive element 33 may extend longitudinally through internal lumen 31 and through shaft 14. As shown in FIG. 1B, fluid delivered through port 22 may surround at least a portion of conductive element 33. In one aspect, conductive element 33 may include one or more layers of insulation to help insulate conductive element 33 from the fluid in internal lumen 31. As alluded to above, a second conductive element (not shown) may be provided as a return pathway where medical device 10 has a bipolar configuration. Although not shown, in another aspect, the energy source may be a part of handle 12 (e.g., an internal battery in handle 12).

As mentioned, handle 12 may control the extension or retraction of electrode 26 relative to the distal end 16 of shaft 14. For example, main body 18 may include a slot 34, and movable body 20 may be slidably positioned within slot 34. For example, main body 18 may be configured to be held by a user's hand, and movable body 20 may be configured to be controlled by the movement of the user's thumb. For example, a side of main body 18 opposite to movable body 20 may include one or more contours 36, which may help the user grip main body 18. Additionally, movable body 20 may include one or more ridges 37, which may help the user manipulate movable body 20. Movable body 20 may be lockable in one or more positions relative to main body 18, and/or may be spring-biased in a direction (e.g., toward a proximally retracted position).

Movable body 20 may be coupled to a drive element, and the drive element may impart distal or proximal movement to at least a portion of electrode 26 based on relative movement between main body 18 and movable body 20. In one aspect, conductive element 33 may also act as a drive wire, rod, cable, or the like, such that conductive element 33 imparts distal or proximal movement to at least a portion of electrode 26 while also coupling electrode 26 to hub 24, e.g., the one or more pins 32, to deliver the energy to (and/or from) electrode 26. As shown in FIG. 1B, movable body 20 may be coupled to conductive element 33 via a coupling mechanism, for example, a coupler 38. In one aspect, coupler 38 may be physically coupled (either directly or indirectly) to movable body 20, and may also be physically coupled (either directly or indirectly) to conductive element 33 such that movement of movable body 20 extends or retracts conductive element 33, and thus extends or retracts electrode 26. It is noted that coupler 38 and/or other components within handle 12 may help maintain the electrical connection between pin 32 and conductive element 33 when conductive element 33, and thus electrode 26, is in the retracted or extended positions. Alternatively, in another aspect, coupler 38 and/or other components within handle 12 may be configured to only electrically connect pin 32 and conductive element 33 when conductive element 33, and thus electrode 26, is in the extended position, or an at least partially extended position.

As shown in FIG. 1A, handle 12 may also include one or more indicators, for example, indicators 39A, 39B. For example, indicators 39A, 39B may visually indicate to the user the position of electrode 26 relative to shaft 14. The position of indicators 39A, 39B may also correspond with the position of movable body 20. For example, indicator 39A may be positioned on handle 12 at a position corresponding with a retracted position of movable body 20, and may indicate that electrode 26 is retracted relative to shaft 14. Similarly, indicator 39B may be positioned on handle 12 at a position corresponding with an extended position of movable body 20, and may indicate that electrode 26 is extended relative to shaft 14.

As shown in FIGS. 1A and 1B, shaft 14 extends from a distal portion of main body 18 to distal end 16, and may surround at least a portion of electrode 26. Shaft 14 may be a sheath that surrounds at least a portion of one or more lumens (e.g., lumen 31) and the drive wire (e.g., conductive element 33). In another aspect, shaft 14 may be an extrusion that includes one or more lumens extending from handle 12 to distal end 16.

The enlarged portion of FIG. 1B illustrates additional features of shaft 14 and distal end 16. Electrode 26 includes insulation tip 28 surrounding a distal portion of electrode shaft 30. Electrode 26 may be positioned within a portion of an end cap 42 of distal end 16. End cap 42 may include a distal end face 44 and graduated surfaces 46, 48, and 50. For example, a first graduated surface 46 may be at a distalmost portion of end cap 42. As shown in FIG. 1B, with shaft 14 coupled to distal end 16, first graduated surface 46 of end cap 42 may be exposed distally beyond shaft 14, while a second graduated surface 48 may be received in shaft 14. A third graduated surface 50 may, for example, be tapered to facilitate insertion of end cap 42 into shaft 14. In another example, shaft 14 may fully enclose the radially exterior portions of end cap 42. End cap 42 may be at least partially electrically insulating. For example, end cap 42 may be formed of a ceramic material or another non-conductive material. Alternatively, only distal end face 44 and an internal portion of end cap 42 that contacts and/or surrounds electrode 26 may be electrically insulating. Distal end face 44 includes a central opening 52 through which electrode 26 may extend and retract.

Electrode 26 may be coupled to a proximal support 54 of distal end 16, which may include a cylindrical extension 56. Proximal support 54 may be coupled to a portion of the drive wire (e.g., conductive element 33) via a drive wire receiving portion 58. Cylindrical extension 56 may extend distally and may receive at least a portion of electrode 26. Electrode 26 and cylindrical extension 56 may be coupled via welding, an adhesive, crimping, friction fit, or other appropriate coupling. In one aspect, cylindrical extension 56 may allow for different electrodes 26 to be removably coupled to distal end 16. Proximal support 54 includes a support lumen 70, and support lumen 70 fluidly connects port 22 to electrode 26, for example, via a lumen (e.g., lumen 31) through shaft 14.

Proximal support 54 includes a proximal coupling portion 72, which includes drive wire receiving portion 58. Drive wire receiving portion 58 may be an indentation that extends parallel to at least a portion of support lumen 70. Drive wire receiving portion 58 may receive a portion of a drive wire (not shown), and the drive wire and/or an inner sheath 40 may be coupled to movable body 20 such that the movement of movable body 20 imparts distal or proximal movement to proximal support 54 and, thus, to electrode 26. The drive wire may be coupled to drive wire receiving portion 58 within coupling portion 72 by welding, an adhesive, crimping, friction fit, or any other permanent or temporary coupling. Proximal support 54 may also be coupled to electrode 26 by welding, an adhesive, crimping, friction fit, or any other permanent or temporary coupling. In one aspect, both the drive wire and proximal support 54 are conductive to electrically connect the one or more prongs 32 of hub 24 to electrode 26. In another aspect, proximal support 54 may be at least partially insulating, and may include a wire or other conductive element electrically connecting the drive wire to electrode 26. Similarly, in one aspect, the drive wire may be at least partially insulating and may include a wire or other conductive element. Furthermore, at least a portion of the drive wire may be positioned within inner sheath 40. Alternatively, the drive wire may be positioned within a separate lumen in shaft 14 (e.g., a lumen separate from the lumen running through inner sheath 40).

End cap 42 includes a central portion 74 through which electrode shaft 30 may move during the extension and retraction. End cap 42 may also include a narrowing portion or stop surface 76 at a distal end of central portion 74. Electrode shaft 30 may include a transition portion 78 between a first longitudinal portion 80 and a second longitudinal portion 82. Stop surface 76 and transition portion 78 may limit the distal extension of electrode 26 through end cap 42. In a fully extended position, first longitudinal portion 80 may protrude from end cap 42 and may form an exposed portion that may be used for cutting or otherwise treating tissue. Additionally, although not shown, end cap 42 may be fixedly coupled to shaft 14 via welding, an adhesive, crimping, friction fit, or other appropriate coupling.

Electrode 26 and proximal support 54 may be movable relative to end cap 42 in response to the relative movement of movable body 20 and main body 18 of handle 12. For example, with movable body 20 in a proximal position relative to main body 18, electrode shaft 30 may be substantially retracted within end cap 42 with only a distal portion of electrode 26 (e.g., insulation tip 28) extending distally beyond end cap 42. Then, as movable body 20 is translated distally relative to main body 18, electrode 26 and proximal support 54 translate distally relative to end cap 42 such that a greater portion of electrode 26 (e.g., electrode shaft 30) extends distally beyond end cap 42 through central opening 52.

Alternatively, although not shown, central opening 52 may be larger than insulation tip 28, and with movable body 20 in the proximalmost position, electrode 26 (including insulation tip 28) may be fully retracted within central opening 52 of end cap 42. Furthermore, in one aspect, movable member 20 may have an equilibrium position relative to main body 18, and the equilibrium position may correspond to electrode shaft 30 being partially extended from end cap 42.

As shown in the enlarged portion of FIG. 1B, electrode shaft 30 includes a distal tip 60 and a longitudinal portion 62. Distal tip 60 and longitudinal portion 62 may be formed by first longitudinal portion 80. Distal tip 60 may be received within insulation tip 28 and covered by insulation tip 28, and longitudinal portion 62 may be proximal to insulation tip 28 and not covered by insulation tip 28.

Electrode shaft 30 also includes an electrode shaft lumen 64 extending through electrode shaft 30, for example, extending longitudinally through a central portion of electrode shaft 30. Electrode shaft lumen 64 may be in fluid communication with port 22 via support lumen 70 through proximal support 54. In one aspect, inner sheath 40 may form at least a portion of the fluid connection between lumen 70 and port 22. Additionally, electrode shaft lumen 64 is in fluid communication with an insulation tip lumen 28C to form a channel to deliver fluid from a distal end of electrode 26.

As shown in FIG. 1B, insulation tip 28 may include a distal end 28A and a side portion 28B. Distal end 28A may be rounded, for example, substantially hemispherical, and side portion 28B may include straight sides, for example, may be substantially cylindrical. In one aspect, the shapes of distal end 28A and side portion 28B may help distal end 16 be atraumatic, and/or may help abut, position, manipulate, or otherwise treat tissue, while electrode 30 may be used to cut, dissect, ablate, mark, coagulate, cauterize, or otherwise treat tissue. Nevertheless, this disclosure is not so limited, and insulation tip 28, including distal end 28A and side portion 28B, may include other shapes. For example, insulation tip 28 may be frustoconical, tapered, chamfered, filleted, beveled, or combinations thereof. In one aspect, insulation tip 28 completely surrounds or covers a distal portion (e.g. distal tip 60) of electrode shaft 30. For example, insulation tip 28 may cover approximately one quarter of a length of first longitudinal portion 80 of electrode shaft 30. In another example, insulation tip 28 may cover approximately one third or one half of the length of first longitudinal portion 80 of electrode shaft 30. In this aspect, insulation tip 28 may provide an insulation from the distal portion of electrode shaft 30 and at least a portion of the tissue near insulation tip 28. For example, insulation tip 28 may abut tissue, and electrode shaft 30 may be energized while insulation tip 28 helps to insulate the tissue that insulation tip 28 abuts against. Moreover, insulation tip 28 may receive distal tip 60 within approximately one half of insulation tip 28 along the longitudinal axis, which may help securely couple insulation tip 28 and electrode 30. Additionally, approximately one half of insulation tip 28 may extend distally beyond distal tip 60, which may help insulate tissue abutting distal portion 28A of insulation tip 28 when electrode 30 is energized.

As discussed below, insulation tip 28 and electrode shaft 30 may be physically coupled, for example, via one or more of soldering, brazing, welding, bonding, or one or more other coupling mechanisms. Moreover, insulation tip 28 and electrode shaft 30 form a fluid channel that extends through both electrode shaft 30 and insulation tip 28 in order to deliver (e.g., inject) fluid to a target site (e.g., within or between layers of tissue to raise, separate, flush, or otherwise treat tissue). Electrode shaft 30 may be energized, and the exposed portion of electrode shaft 30 (e.g., longitudinal portion 62) may be used to cut, dissect, ablate, mark, coagulate, cauterize, or otherwise treat tissue.

Figure 2A:
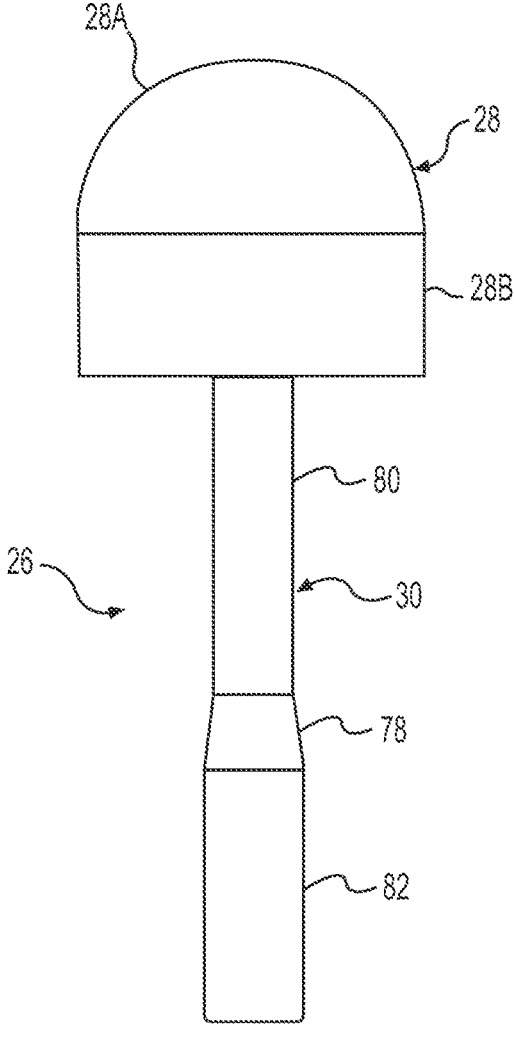
FIG. 2A illustrates a side view of an electrode portion of the medical device of FIGS. 1A and 1B.
Figure 2B:
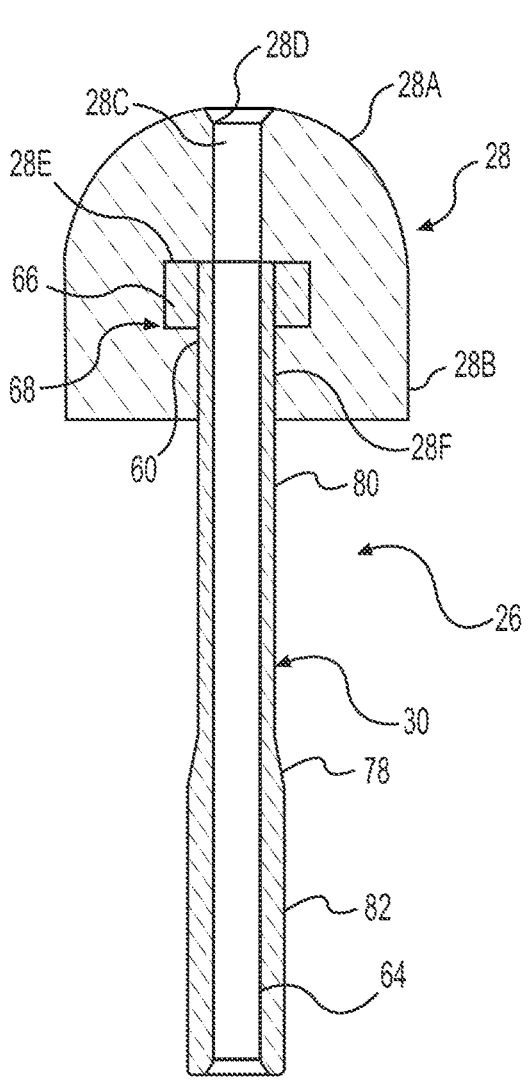
FIG. 2B illustrates a cross-sectional view of the electrode portion of FIG. 2A, according to aspects of the disclosure.

FIGS. 2A and 2B illustrate additional aspects of electrode 26 that may form a portion of distal end 16 of medical device 10. FIG. 2A shows a side view of electrode 26, and FIG. 2B shows a cross-sectional view of electrode 26. As mentioned, electrode 26 includes insulation tip 28 surrounding electrode shaft 30. Insulation tip 28 may include distal portion 28A and side portion 28B. As shown in FIGS. 1B and 2B, insulation tip 28 includes insulation tip lumen 28C. In this aspect, fluid delivered through electrode shaft lumen 64 may be delivered distally through insulation tip lumen 28C. In one aspect, electrode shaft lumen 64 and insulation tip lumen 28C may be approximately the same size. In another aspect, electrode shaft lumen 64 and insulation tip lumen 28C may be tapered distally such that distal portions of the lumens are narrower than proximal portions of the lumens. Alternatively, electrode shaft lumen 64 and insulation tip lumen 28C may be tapered proximally such that proximal portions of the lumens are narrower than distal portions of the lumens. In these aspects, varying sizes of electrode shaft lumen 64 and insulation tip lumen 28C may help increase or decrease the pressure of the fluid being delivered through the fluid channel. A distal end portion 28D of insulation tip lumen 28C may include a chamfer or angled portion, which may help disperse, direct, or otherwise deliver fluid to a target site with a decreased likelihood of damaging tissue. Additionally, distal end 28A of insulation tip 28 may include an internal face 28E. When insulation tip 28 and electrode 30 are coupled together, the distal end face of electrode 20 may abut internal face 28E.

Figures 4A, 4B, 4C:
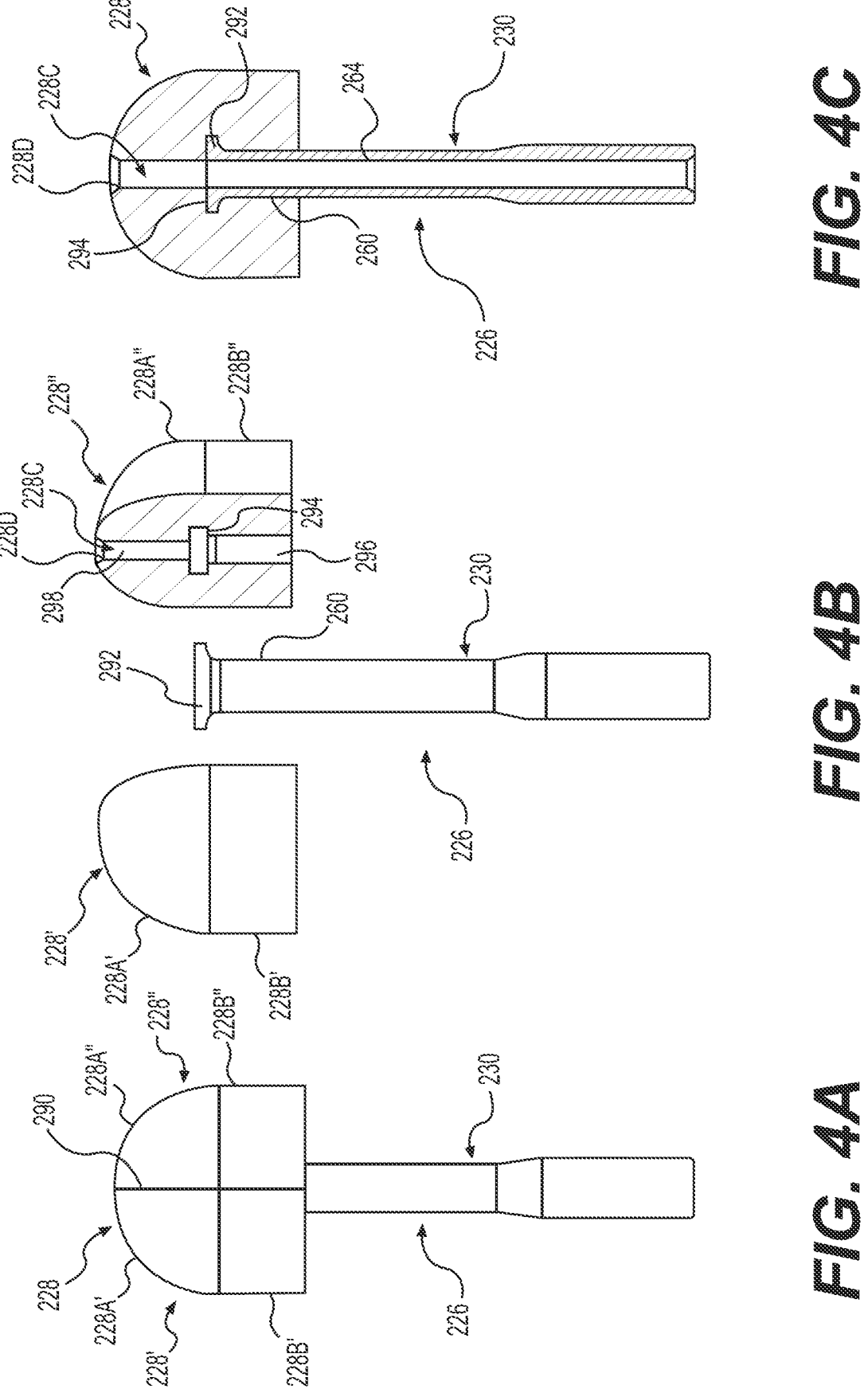
FIG. 4A illustrates a side view of a further alternative exemplary electrode portion of the medical device of FIGS. 1A and 1B, according to aspects of the disclosure.
FIG. 4B illustrates a partially exploded view of the electrode portion of FIG. 4A.
FIG. 4C illustrates a cross-sectional view of the electrode portion of FIG. 4A.

As mentioned, electrode shaft 30 may include transition portion 78, first longitudinal portion 80, and second longitudinal portion 82. In one aspect, a distal portion (e.g., first longitudinal portion 80) of electrode shaft 30 may include a consistent width. In another aspect, and as shown in FIGS. 4B and 4C, the distal end of the distal portion of electrode shaft 30 may include an increased thickness (e.g., a widened end portion 292) relative to the remaining distal portion of electrode shaft 30.

As shown in FIG. 2B, insulation tip 28 may be coupled to a distal portion of electrode shaft 30 via a solder 66. In one aspect, insulation tip 28 may include a gap 68 for example, a radial indentation or cutout, in a radial internal portion 28F of insulation tip 28. Gap 68 may occupy approximately a quarter of a longitudinal length of insulation tip 28. In this aspect, insulation tip 28 may be coupled to electrode shaft 30 by placing melted solder 66 in gap 68, and then inserting electrode shaft 30 into insulation tip 28. The solder 66 may help couple insulation tip 28 and electrode shaft 30. Additionally, as shown in FIG. 2B, radial internal portion 28F that forms insulation tip lumen 28C may transition from a wider proximal lumen (e.g., where insulation tip 28 overlaps with electrode shaft 30) to a narrower distal lumen (e.g., wherein insulation tip 28 does not overlap with electrode shaft 30). In this aspect, the transition may correspond to the distal end of gap 68, and may also help form a stop surface for the distal end face of distal tip 60 to abut internal face 28E of insulation tip 28.

Insulation tip 28 may be formed of a ceramic (e.g., zirconia, an alloy containing zirconium (e.g., $ZrO_2$), aluminum oxide ($Al_2O_3$), a ceramic alloy, etc.) a polymer material (e.g., a fluoropolymer, polyether ether ketone (PEEK), etc.) or another medically-safe, heat-resistant, and non-conductive material. Electrode shaft 30 may be formed of a conductive material, for example, a stainless steel (e.g., 316L stainless steel), titanium, or another medically-safe and conductive material. In one aspect, electrode shaft 30 may include a surface finish, for example, may be passivated per ASTM A967 Nitric 2.

Although not shown, electrode 26 may include an electrode plate. The electrode plate may be positioned at the proximal face of side portion 28B and/or may surround a portion of electrode shaft 30 just proximal to insulation tip 28. In one aspect, the electrode plate may be conductive, and may be energized when electrode shaft 30 is energized. In another aspect, the electrode plate may not be conductive. In either aspect, the electrode plate may help support insulation tip 28 and/or electrode shaft 30, and/or may help couple insulation tip 28 to electrode shaft 30.

Various portions of insulation tip 28 may include heights and width, for example, as measured relative to a longitudinal axis of insulation tip 28. Insulation tip 28 may include a width (e.g., at a proximal end of side portion 28B) of approximately 2.0 to 3.0 mm, for example, approximately 2.2 mm. Insulation tip 28 may have a height (e.g., from the proximal end of side portion 28B to a distal end face of distal end 28A) of approximately 2.0 to 3.0 mm, for example, approximately 2.1 mm. For example, distal end 28A of insulation tip 28 may be rounded (e.g., substantially hemispherical), and may include a radius of approximately 0.5 to 2.0 mm, for example, approximately 1.1 mm. In another aspect, and as discussed in detail below with respect to FIGS. 6A-6C and 7A-7C, insulation tip 28 may include a cylindrical tip portion or another shape. Side portion 28B may have a height of approximately 0.5 to 1.0 mm, for example, approximately 0.9 mm. If electrode 26 includes the electrode plate (not shown), the electrode plate may include a height of 0.05 to 0.2 mm, for example, approximately 0.1 mm.

Additionally, as shown in FIG. 2B, the wider portion of insulation tip lumen 28C formed by radial internal portion 28F (e.g., where insulation tip 28 overlaps with electrode shaft 30) may include a height of approximately 0.5 to 1.5 mm, for example, approximately 1.0 mm, and the narrower portion of insulation tip lumen 28C (e.g., wherein insulation tip 28 does not overlap with electrode shaft 30) may include a height of approximately 0.5 to 1.5 mm, for example, approximately 1.0 mm. The wider portion of insulation tip lumen 28C formed by radial internal portion 28F (e.g., where insulation tip 28 overlaps with electrode shaft 30) may include a width of approximately 0.3 to 0.7 mm, for example, approximately 0.5 mm, and the narrower portion of insulation tip lumen 28C (e.g., wherein insulation tip 28 does not overlap with electrode shaft 30) may include a width of approximately 0.2 to 0.5 mm, for example, approximately 0.3 mm. As mentioned, distal end portion 28D may include a chamfer or angled portion, which may transition from the width of the narrowed lumen, for example, approximately 0.3 mm, to a wider width, for example, approximately 0.37 mm. In this aspect, the chamfer or angled portion of distal portion 28D may include an angle of approximately 60 degrees relative to the longitudinal axis.

Various portions of electrode shaft 30 may include heights and width, for example, as measured relative to a longitudinal axis of electrode shaft 30. Electrode shaft 30 may include a total height of approximately 4.0 to 6.0 mm, for example, approximately 5.2 mm. First longitudinal portion 80 may include a height of approximately 2.0 to 4.0 mm, for example, approximately 3.0 mm. Second longitudinal portion 82 may include a height of approximately 1.0 to 2.0 mm, for example, approximately 1.7 mm. Transition portion 78 may include a height of approximately 0.2 to 1.0 mm, for example, approximately 0.5 mm. First longitudinal portion 80 may include a width of approximately 0.4 to 0.7 mm, for example, approximately 0.5 mm. Second longitudinal portion 82 may include a width of approximately 0.5 to 0.7 mm, for example, approximately 0.6 mm. In this aspect, transition portion 78 may include an angle of approximately 7 degrees relative to the longitudinal axis. In one aspect, electrode shaft lumen 64 and insulation tip lumen 28C may be approximately the same width (e.g., in a direction transverse to the longitudinal axes of electrode shaft lumen 64 and insulation tip lumen 28C). For example, electrode shaft lumen 64 and insulation tip lumen 28C may include constant widths of approximately 0.3 mm. In this aspect, second longitudinal portion 82 may include a radial thickness (e.g., from a radial exterior to a radial interior that defines electrode shaft lumen 64) of approximately 0.5 mm, and first longitudinal portion 80 may include a radial thickness (e.g., from a radial exterior to a radial interior that defines electrode shaft lumen 64) of approximately 0.3 mm.

FIGS. 3A and 3B illustrate views of another electrode 126 similar to electrode 26, with similar elements shown by 100 added to the reference numbers. As shown, electrode 126 includes an insulation tip 128 and an electrode shaft 130. Insulation tip 128 may include a distal portion 128A, which may be rounded, and a side portion 128B, which may be cylindrical. In the aspect shown in FIGS. 3A and 3B, insulation tip 128 and electrode shaft 130 may be coupled via brazing, for example, by melting and flowing (e.g., by capillary action) a filler metal (e.g., aluminum-silicon, copper, copper-silver, copper-zinc (brass), copper-tin (bronze), gold, gold-copper, gold-nickel, gold-chrome, gold-silver, a nickel alloy, silver, an amorphous brazing foil using nickel, iron, copper, silicon, boron, phosphorous, and/or other materials) between insulation tip 128 and electrode shaft 130. The brazing may also include an initial step of sputtering insulation tip 128 with a material that helps bonding (e.g., Cr. Mo, Ti, etc.). Insulation tip 128 and electrode shaft 130 may also be joined by using an ink (e.g., moly-manganese based inks) and then applying the filler material, by using an active brazing alloy, etc. Once insulation tip 128 and electrode shaft 130 are coupled, insulation tip 128 and electrode shaft 130 form a fluid channel through an electrode shaft lumen 164 and an insulation tip lumen 128C in order to deliver fluid to a target site, as discussed above. Moreover, the exposed portion of electrode shaft 130 may be energized to treat tissue, while insulation tip 128 covers and insulates the distal portion of electrode shaft 130, which may help prevent or minimize damage and/or unintended contact with tissue.

The filler metal (not shown) may have a lower melting point than the materials that form insulation tip 128 and electrode shaft 130. In one aspect, insulation tip 128 may be placed over the distal portion of electrode shaft 130 (or electrode shaft 130 may be inserted into insulation tip 128) such that electrode shaft 130 abuts internal face 128E of insulation tip 128. Then, the filler metal, which has been heated, for example, to a temperature slightly above its melting temperature (e.g., its liquidus temperature), may be flowed over the outer face of electrode shaft 130 and/or the internal face of insulation tip 128. In another example, the filler metal may be flowed over the outer face of electrode shaft 130 and/or the internal face of insulation tip 128, and then insulation tip 128 may be placed over the distal portion of electrode shaft 130 (or electrode shaft 130 may be inserted into insulation tip 128) such that electrode shaft 130 abuts internal face 128E of insulation tip 128. In the above aspects, the cooling of the filler metal helps to physically couple insulation tip 128 and electrode shaft 130.

It is noted that, in the aspects shown in FIGS. 3A and 3B, insulation tip 128 may not include a gap 68, as in insulation tip 28 of FIGS. 2A and 2B. Instead, the filler metal may couple an internal face of insulation tip lumen 28C to an outer face of electrode 130 at a junction 184. In this aspect, junction 184 (or a space between the internal face of insulation tip lumen 28C and the outer face of electrode shaft 130 that is filled by the filler material) may be approximately 0.1 mm or less, for example, approximately 0.03 to 0.08 mm.

FIGS. 4A-4C illustrate views of another electrode 226 similar to electrode 26, with similar elements shown by 200 added to the reference numbers. As shown, electrode 226 includes an insulation tip 228 and an electrode shaft 230.

Insulation tip 228 may be formed of two halves 228', 228". Half 228' may include a partially-rounded distal portion 228A' (e.g., a quarter of a sphere) and a partially cylindrical side portion 228B', and half 228" may include a partially-rounded distal portion 228A" (e.g., a quarter of a sphere) and a partially-cylindrical side portion 228B". Halves 228', 228" may be divided along a longitudinal centerline 290. For example, as shown in FIG. 4B, halves 228', 228" may be separated. Halves 228', 228" may be positioned around the distal portion (e.g., distal tip 260) of electrode shaft 230 and may be bonded or joined together, for example, via soldering (which, although not shown, may include one or more gaps to receive the solder, as discussed with respect to FIGS. 2A and 2B), brazing as discussed with respect to FIGS. 3A and 3B, welding, one or more adhesives, or any other coupling mechanism. In one aspect, joining halves 228', 228" around the distal portion of electrode shaft 230 may also couple halves 228', 228" (and thus insulation tip 228) to electrode shaft 230. Alternatively or additionally, halves 228', 228", either individually or together, may be joined to electrode shaft 230 via any of the aforementioned coupling mechanisms.

In one aspect, as shown in FIGS. 4B and 4C, the distal end of electrode shaft 230 may include widened end portion 292. Halves 228', 228" of insulation tip 228 may each include grooves 294 to receive at least a portion of widened end portion 292. For example, widened end portion 292 may be a generally cylindrical extension that extends radially outward relative to a longitudinal axis of electrode 230. In one aspect, widened end portion 292 may include a flat distal end and a curved proximal end. Halves 228', 228" of insulation tip 228 may each include a groove 294 to receive respective portions (e.g., halves) of widened end portion 292. Each groove 294 in halves 228', 228" may include a shape corresponding to the shape of widened end portion 292.

Insulation tip 228 (as formed by joined halves 228', 228") may include an insulation tip lumen 228C with a proximal portion 296 and a distal portion 298. Grooves 294 may be positioned between proximal portion 296 and distal portion 298. Proximal portion 296 may be wider than distal portion 298. As shown in FIGS. 4B and 4C, groove 294 may be wider (e.g., extend further radially away from the longitudinal axis of insulation tip 228) than proximal portion 296. Distal portion 298 may be approximately the same width as an electrode shaft lumen 264, and distal portion 298 and electrode shaft lumen 264 may form a fluid channel. Moreover, insulation tip lumen 228C may terminate distally at the distal end portion 228D, which may include a chamfer or angled portion, as mentioned above. Groove 294, proximal portion 296, and distal portion 298 may be sized to accommodate any shape or configuration of electrode 230, such that distal tip 260 is receivable into insulation tip 228. Additionally, in some aspects, portions of insulation tip 228

(e.g., groove 294 and proximal portion 296) may be sized to form a space between overlapping portions of insulation tip 228 and electrode 230, for example, to help accommodate for differences in coefficients of thermal expansion between the materials of insulation tip 228 and electrode 230.

Once insulation tip 228 and electrode shaft 230 are coupled, insulation tip 228 and electrode shaft 230 form the fluid channel through electrode shaft lumen 264 and insulation tip lumen 228C in order to deliver fluid to a target site and/or to tissue from the distal end of electrode 226, as discussed above. Moreover, the exposed portion of electrode shaft 230 may be energized to treat tissue, while insulation tip 228 covers the distal portion (e.g., distal tip 260) of electrode shaft 230, which may help prevent or minimize damage and/or unintended contact with tissue.

Figure 5B:
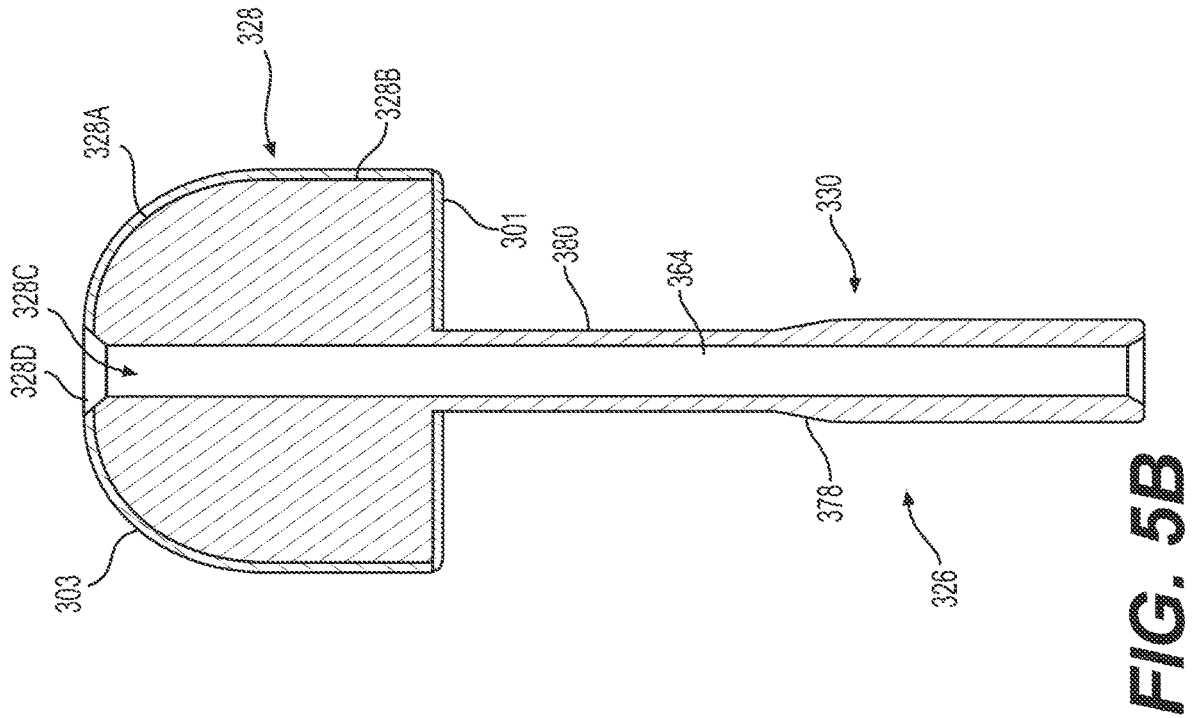
FIG. 5B illustrates a cross-sectional view of the electrode portion of FIG. 5A, according to aspects of the disclosure.
Figure 5A:
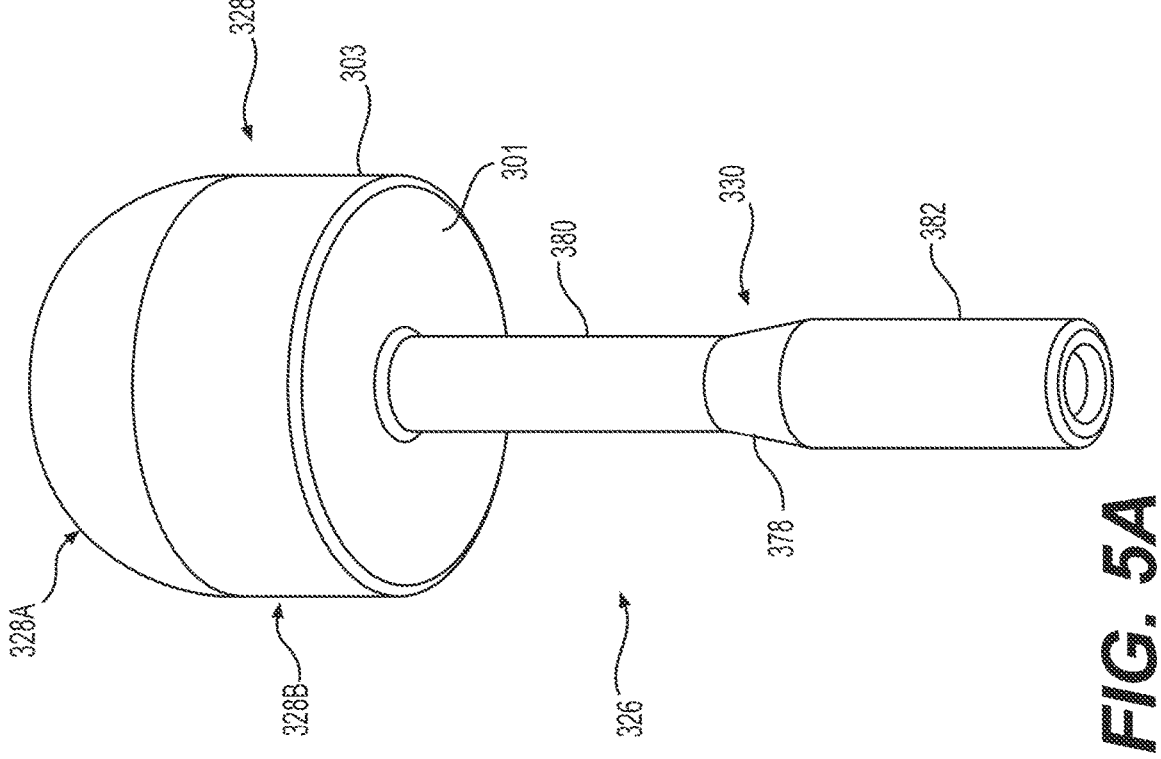
FIG. 5A illustrates a perspective view of another alternative exemplary electrode portion of the medical device of FIGS. 1A and 1B.

FIGS. 5A and 5B illustrate views of another electrode 326 similar to electrode 26, with similar elements shown by 300 added to the reference numbers. As shown, electrode 326 includes a tip 328 and an electrode shaft 330, which may be similarly sized and shaped as the insulation tips and electrode shafts discussed above. For example, tip 328 may include a distal portion 328A and a side portion 328B. Moreover, an insulating layer 303 may cover at least a portion of tip 328, forming an exterior of tip 328. It is noted that, in the aspects discussed below, tip 328 (other than insulating layer 303) may be formed of a conductive material, and insulating layer 303 may include an insulative material and may insulate at least a portion of tip 328, and thus also insulate a distal portion of electrode 326.

Electrode shaft 330 may include a tapered transition portion 378 between a first longitudinal portion 380 and a second longitudinal portion 382. First longitudinal portion 380 has a smaller outer diameter than second longitudinal portion 382, and first longitudinal portion 380 and second longitudinal portion 382 may have the same inner diameter. Additionally, electrode 326 may include an electrode plate 301 positioned at the proximal face of side portion 328B and surrounding a portion of electrode shaft 330. Electrode plate 301 may be substantially circular and cover an entirety of the proximal end face of tip 328, or may cover a portion of the proximal end face of tip 328. Electrode plate 301 may be conductive, and may be energized when electrode shaft 330 is energized, as discussed above.

As shown in FIG. 5B, tip 328 includes a tip lumen 328C, and electrode shaft 330 includes an electrode shaft lumen 364. Fluid may be delivered through electrode shaft lumen 364 and tip lumen 328C to deliver fluid distally, for example, from a distal end portion 328D, as discussed above. It is noted that, even with insulating layer 303 covering at least a portion of tip 328, insulating layer 303 does not cover distal end portion 328D.

As shown in FIG. 5B, a portion of tip 328 (not including insulating layer 303) and electrode shaft 330 may be formed of a single piece of material, for example, stainless steel. Alternatively, although not shown, a portion of tip 328 and electrode shaft 330 may be different pieces of material, for example, different pieces of metal(s), and tip 328 and electrode shaft 330 may be welded (e.g., laser welded) together or otherwise coupled together. In one aspect, forming the portion of tip 328 and electrode shaft 330 out of the same material may help to prevent and/or reduce a chance of failure between the connection of tip 328 and electrode shaft 330 by, for example, a ceramic insulation tip becoming disconnected from a metallic electrode shaft. In another aspect, welding tip 328 and electrode shaft 330 together may also help to prevent and/or reduce a chance of failure between the connection of tip 328 and electrode 330.

Insulating layer 303 may be deposited on the exterior of a portion of tip 328. For example, insulating layer 303 may be deposited via physical vapor deposition (e.g., sputtering), chemical vapor deposition, micro-arc oxidation, sol-gel coating, thermal spraying (e.g., cold spray coating, warm spray coating, arc wire spray coating), electrodeposition, electrolytic deposition, electrophoretic deposition, high-velocity oxy-fuel coating, plasma spray coating, powder coating and glazing, laser-based deposition of one or more powders, or another coating mechanism. Insulating layer 303 may be approximately 0.5 to 500 microns thick, for example, approximately 300 microns thick. In one aspect, the thickness of insulating layer 303 may be at least partially based on the dielectric properties of the insulating material, breakdown voltage requirements, and/or one or more other parameters. For example, a minimum thickness of insulating layer 303 may be approximately equal to a maximum applied voltage divided by a dielectric breakdown strength of the material. In this example, alumina includes a dielectric breakdown strength of approximately 13.4 MV/m (or 13.4 V/micron). Accordingly, if electrode 326 is configured to and/or capable of delivering a maximum voltage of approximately 5000 volts, then a minimum thickness for insulating layer 303 would be approximately 373 microns. Similarly, if electrode 326 is configured to and/or capable of delivering a maximum voltage of approximately 500 volts, then a minimum thickness for insulating layer 303 would be approximately 37.3 microns.

Insulating layer 303 may insulate at least a portion of tip 328 when electrode shaft 330 (including the internal portion of tip 328) is energized. In one aspect, as shown in FIGS. 5A and 5B, insulating layer 303 may be deposited over an entirety of a portion of tip 328, forming an exterior of tip 328, except for the proximal end face of tip 328. In another aspect, although not shown, insulating layer 303 may be deposited on only a distal portion, for example, distal end 328A of tip 328. In yet another aspect, although not shown, insulating layer 303 may be deposited over an entirety of a portion of tip 328, forming an exterior of tip 328, including the proximal end face of tip 328. In these aspects, electrode 326 may not include electrode plate 301, or electrode plate 301 may be positioned proximal of the insulating layer 303 on the proximal end face of tip 328.

Insulating layer 303 may be formed of ceramic (e.g., zirconia, an alloy containing zirconium (e.g., $ZrO_2$), aluminum oxide ($Al_2O_3$), a ceramic alloy, etc.). Alternatively or additionally, insulating layer 303 may be formed of a polymer material (e.g., a fluoropolymer, polyether ether ketone (PEEK), etc.) or another biocompatible, heat-resistant, and non-conductive material, such as, for example, a glass (silicone-based, boron-based, etc.).

Figures 6A, 6B, 6C:
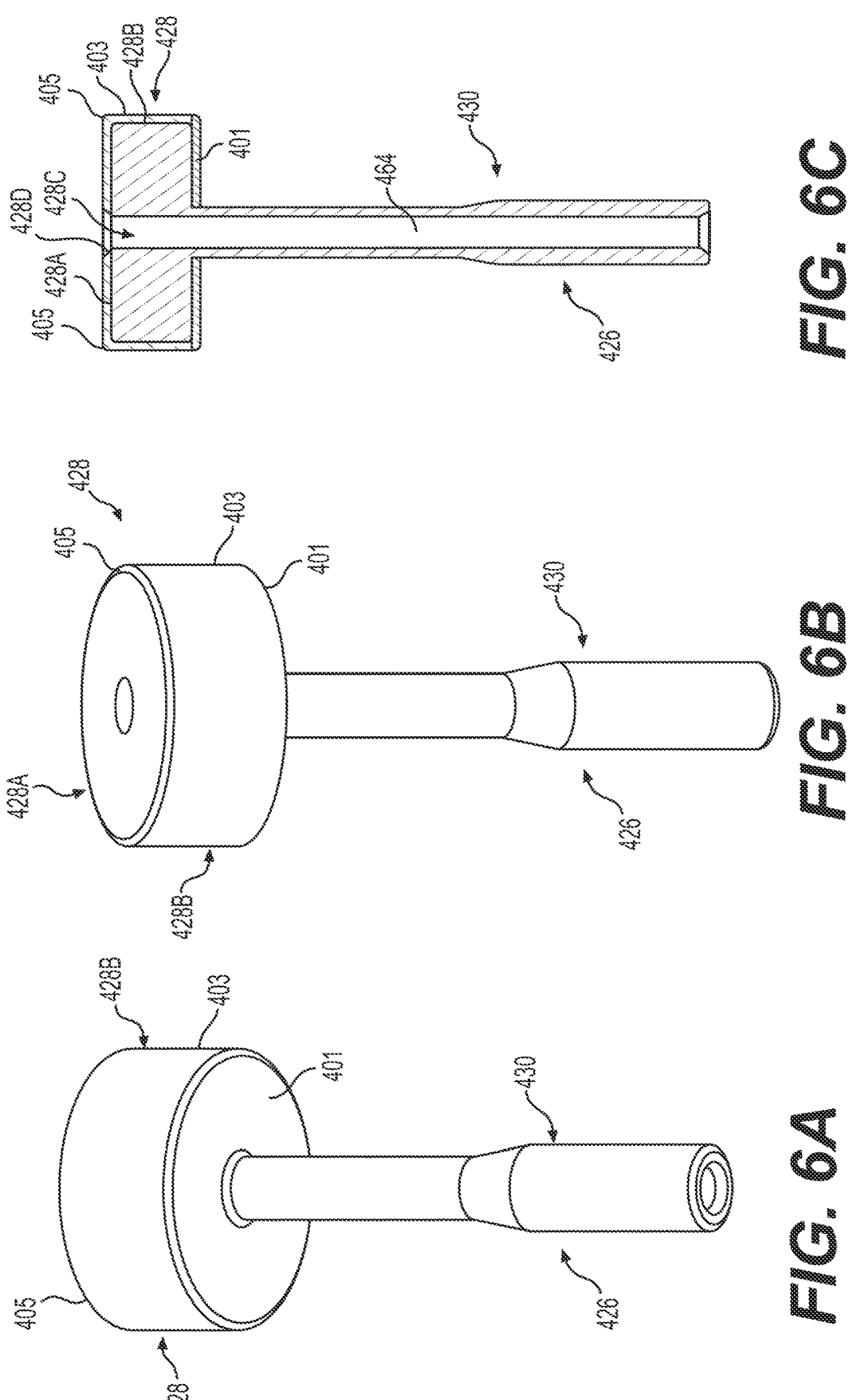
FIGS. 6A and 6B illustrate perspective views of a further alternative exemplary electrode portion of the medical device of FIGS. 1A and 1B, according to aspects of the disclosure.
FIG. 6C illustrates a cross-sectional view of the electrode portion of FIGS. 6A and 6B.

FIGS. 6A-6C illustrate views of another electrode 426 similar to electrode 26, with similar elements shown by 400 added to the reference numbers. As shown, electrode 426 includes a tip 428 and an electrode shaft 430. Electrode shaft 430 may be similarly sized and shaped as discussed above. Additionally, electrode 426 may include an electrode plate 401 positioned at the proximal face of tip 428. As shown, tip 428 may be substantially cylindrical. For example, tip 428 may include a distal face 428A and a side portion 428B. An insulating layer 403 may cover at least a portion of tip 428, forming an exterior layer of tip 428.

As discussed above, at least a portion of tip 428 and electrode shaft 430 may be formed of the same piece of material, or may be coupled together (e.g., via laser welding). As shown in FIG. 6C, tip 428 includes a tip lumen 428C, and electrode shaft 430 includes an electrode shaft lumen 464. Fluid may be delivered through electrode shaft lumen 464 and tip lumen 428C to deliver fluid distally, for example, from a distal end portion 428D, as discussed above. Moreover, insulating layer 403 may cover and insulate at least a portion of tip 428, as discussed above. Distal corners 405 of insulating layer 403 may be atraumatic, for example, rounded or otherwise smoothed, to help prevent or minimize damage to tissue. Alternatively, although not shown, at least a portion of the distal end face of tip 428 may not include insulating layer 403, to expose conductive material of tip 428. For example, a portion of distal face 428A may not include insulating layer 403.

In one aspect, tip 428 may comprise approximately one eighth to one quarter of the entire height of electrode 426. For example, electrode 426 may include a total height of approximately 4.0 to 6.0 mm, for example, approximately 5.2 mm, and tip 428 may include a total height of approximately 0.5 to 1.5 mm, for example, approximately 0.9 mm. Electrode shaft 430 may comprise the remaining height of electrode 426.

Figure 7C:
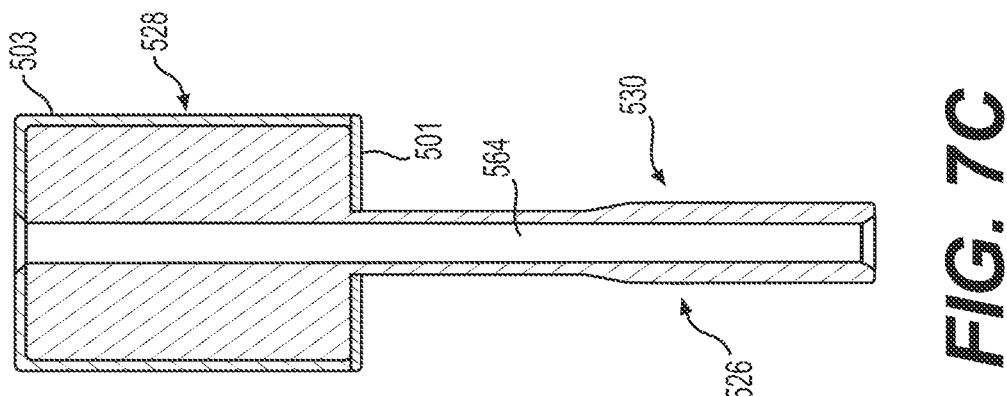
FIG. 7C illustrates a cross-sectional view of the electrode portion of FIGS. 7A and 7B.
Figure 7B:
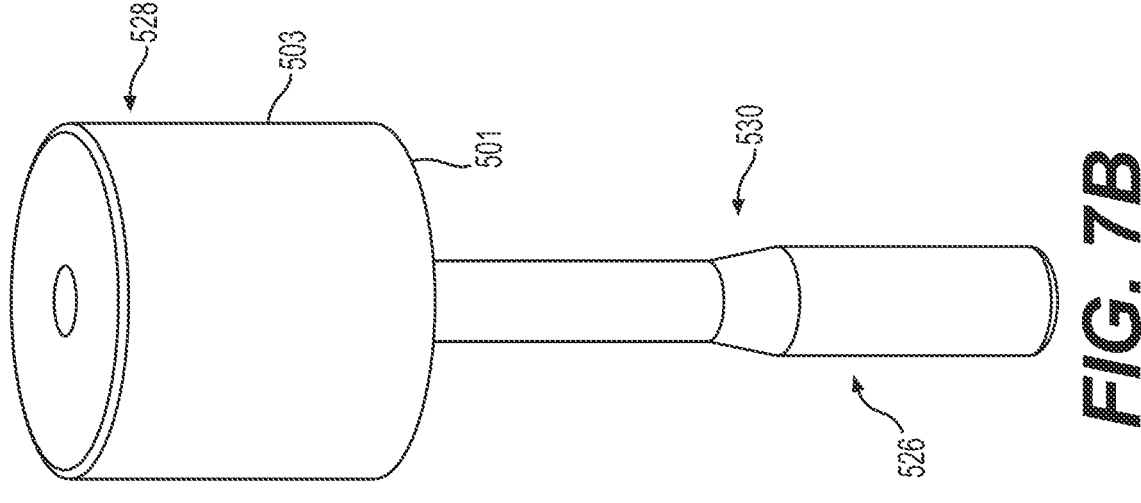
FIGS. 7A and 7B illustrate perspective views of a further alternative exemplary electrode portion of the medical device of FIGS. 1A and 1B, according to aspects of the disclosure.
Figure 7A:
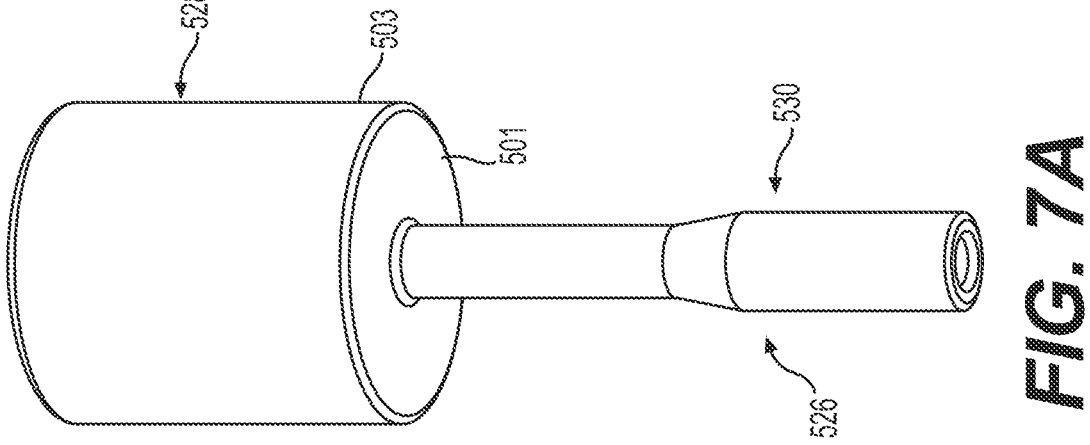

FIGS. 7A-7C illustrate views of another electrode 526 similar to electrode 26, with similar elements shown by 500 added to the reference numbers. As shown, electrode 526 includes a tip 528 and an electrode shaft 530. Electrode shaft 530 may be similarly sized and shaped as discussed above. Additionally, electrode 526 may include an electrode plate 501 positioned at the proximal face of tip 528. As shown, tip 528 may be substantially cylindrical. For example, tip 528 may include a distal face 528A and a side portion 528B. An insulating layer 503 may cover at least a portion of tip 528, forming an exterior layer of tip 528.

Additionally, tip 528 may be larger, for example, with a greater height in the longitudinal direction than tip 428. For example, electrode 526 may include a total height of approximately 4.0 to 6.0 mm, for example, approximately 5.2 mm, and tip 528 may include a total height of approximately 1.0 to 3.0 mm, for example, approximately 2.0 mm. Electrode shaft 530 may comprise the remaining height of electrode 526. As a result, tip 528, with insulating layer 503 forming the exterior layer of tip 528, may insulate a larger portion of electrode 526, may extend farther distally from the distal end of shaft 14 when coupled to medical device 10, and/or may extend farther distally beyond electrode shaft 530. One or more of these features may help insulate tissue from electrode 526 when electrode 526 is energized.

Figure 8:
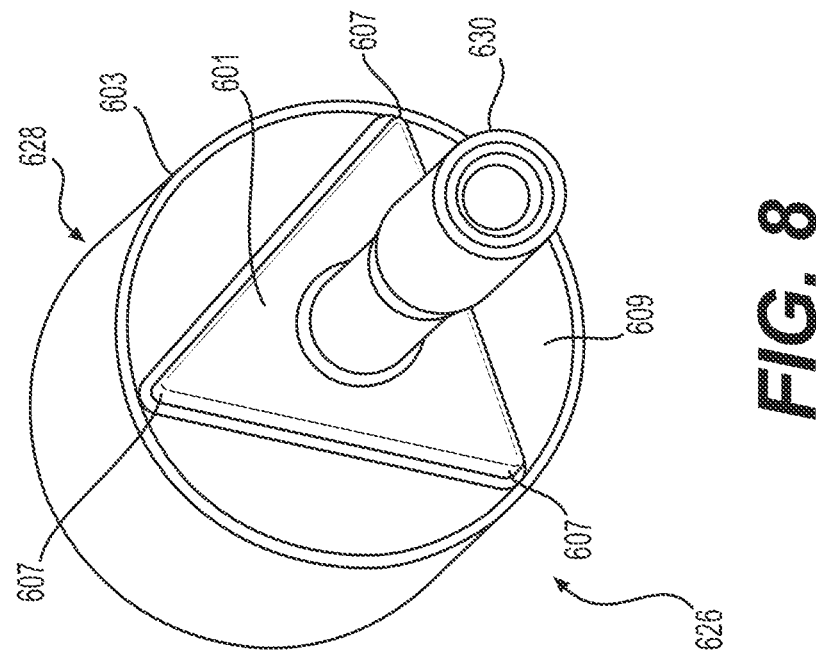
FIG. 8 illustrates a perspective view of another alternative exemplary electrode portion of the medical device of FIGS. 1A and 1B, according to aspects of the disclosure.

FIG. 8 illustrates another electrode 626 similar to electrode 26, with similar elements shown by 600 added to the reference numbers. As shown, electrode 626 includes a tip 628 and an electrode shaft 630. As discussed above, an insulating layer 603 may cover at least a portion of tip 628, forming an exterior layer of tip 628. Furthermore, electrode 626 includes an electrode plate 601.

As shown, electrode plate 601 may be substantially triangular, for example, including three points 607. Points 607 of electrode plate 601 may be rounded, which may help prevent or minimize damage to tissue. Additionally, electrode plate 601 may be an equilateral triangle (as shown) or may be another arrangement, for example, with two points 607 closer together, as compared to the spacing of those two points 607 to a third point 607. As shown in FIG. 8, points 607 may be substantially aligned with edges of tip 628. In this manner, with tip 628, including insulating layer 603 forming the exterior of tip 628, and with the edges of tip 628 abutting tissue, one or more points 607 may contact tissue when electrode 630, and thus electrode plate 601, is energized, for example, to mark tissue. Alternatively, one or more points 607 may be radially within edges of tip 628, which may help insulate tissue contacting tip 628. In these aspects, an exposed proximal portion 609 of tip 628 may be coated (e.g., by sputtering) with insulating layer 603 forming the exterior of tip 628 on proximal portion 609.

Figure 9:
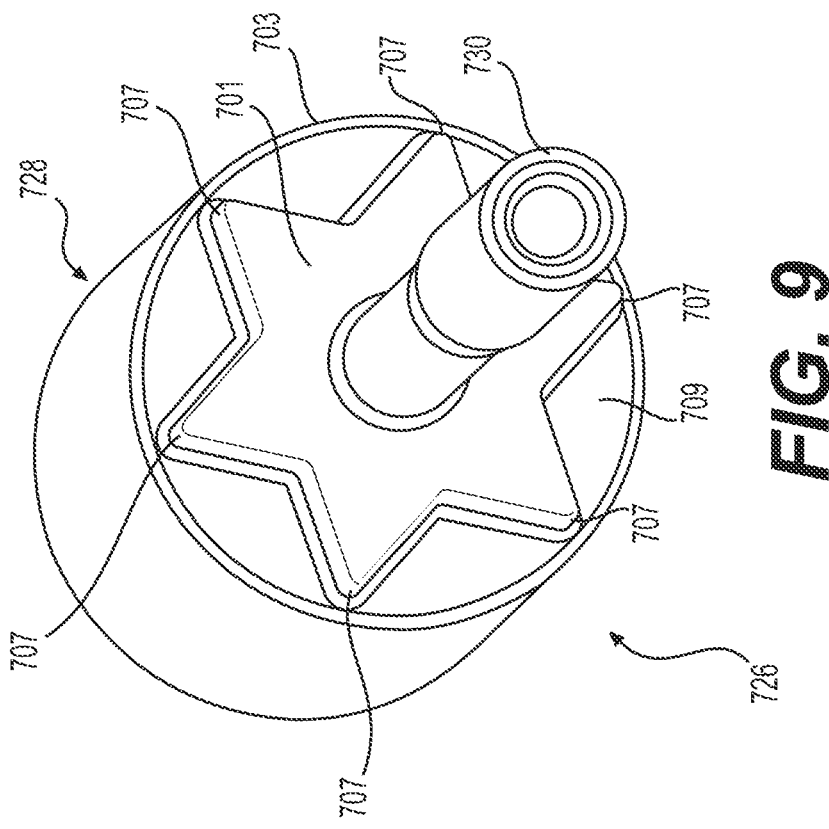
FIG. 9 illustrates a perspective view of a further alternative exemplary electrode portion of the medical device of FIGS. 1A and 1B, according to aspects of the disclosure.

FIG. 9 illustrates another electrode 726 similar to electrode 26, with similar elements shown by 700 added to the reference numbers. As shown, electrode 726 includes a tip 728 and an electrode shaft 730. As discussed above, an insulating layer 703 may cover at least a portion of tip 728, forming an exterior layer of tip 728. Furthermore, electrode 726 includes an electrode plate 701.

As shown, electrode plate 701 may be substantially star-shaped, for example, including five, six (as shown), seven, or more points 707. Additionally, electrode plate 701 may be a star-shape with points 707 evenly spaced apart (as shown) or may be another arrangement, for example, with two or more points 707 positioned closer together, as compared to spacings of other points 707. Points 707 of electrode plate 701 may be rounded, which may help prevent or minimize damage to tissue. As shown in FIG. 9, points 707 may be substantially aligned with edges of tip 728. In this manner, with tip 728, including insulating layer 703 forming the exterior of tip 728, and with the edges of tip 728 abutting tissue, one or more points 707 may contact tissue when electrode 730, and thus electrode plate 701, is energized, for example, to mark tissue. Alternatively, one or more points 707 may be radially within edges of tip 728, which may help insulate tissue contacting tip 728. In these aspects, an exposed proximal portion 709 of tip 728 may be coated (e.g., by sputtering) with insulating layer 703 forming the exterior of tip 728 on proximal portion 709.

Electrode plates 601 and 701 may be coupled to any of the electrodes discussed herein. As mentioned, electrodes plates 601 and 701 may be conductive, and may be energized when the respective electrode is energized. In addition to the electrode plates 601 and 701 discussed above, it is contemplated that any of the electrodes disclosed herein may include various shapes of electrode plates. For example, although not shown, an electrode may include a square electrode plate, a pentagonal electrode plate, a hexagonal electrode plate, etc.

Figure 10B:
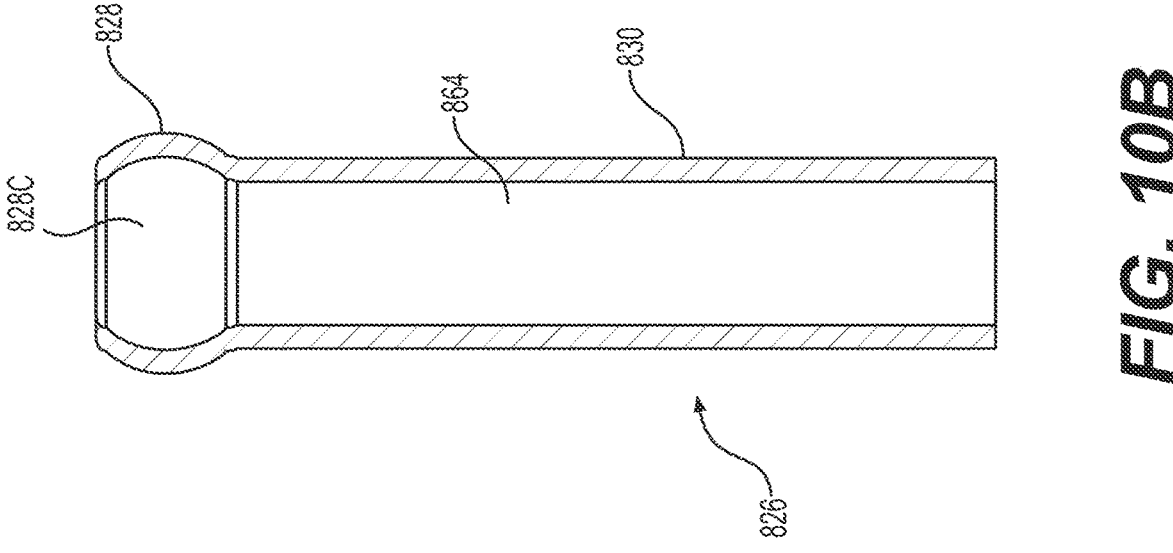
FIG. 10B illustrates a cross-sectional view of the electrode portion of FIG. 10A, according to aspects of the disclosure.
Figure 10A:
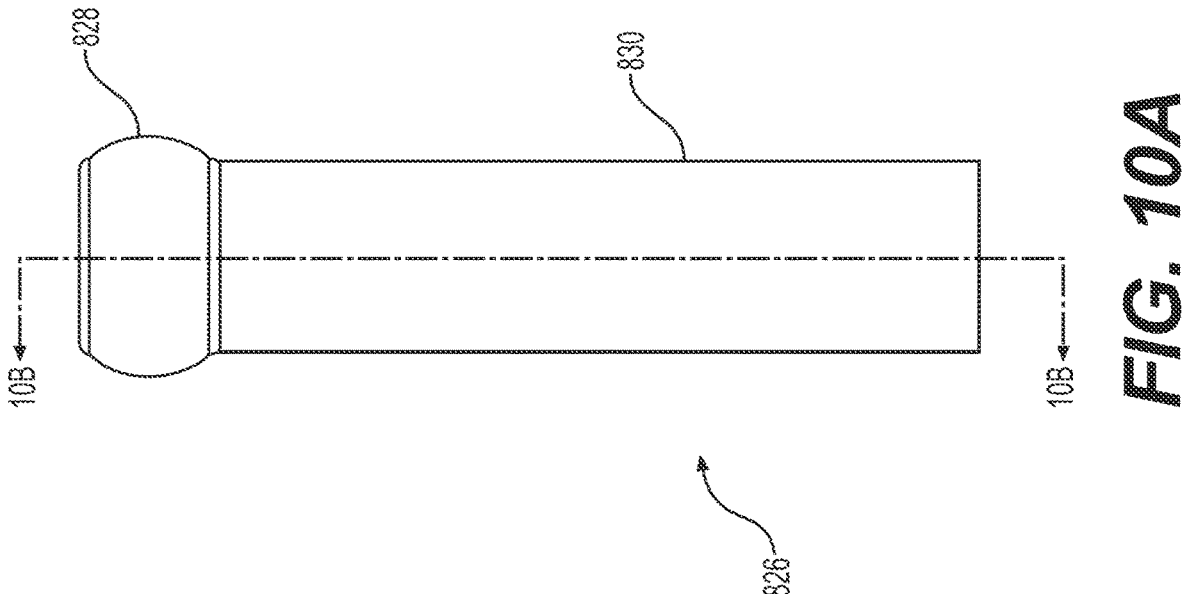
FIG. 10A illustrates a side view of another alternative exemplary electrode portion of the medical device of FIGS. 1A and 1B.

FIGS. 10A and 10B illustrate another alternative electrode 826 similar to electrode 26, with similar elements shown by 800 added to the reference numbers. Electrode 826 includes a tip 828 and an electrode shaft 830. As shown in FIG. 10B, electrode 826 includes a fluid delivery channel formed by an electrode shaft lumen 864 and a tip lumen 828C. In one aspect, tip 828 may be partially spherical (e.g., partially circular in the cross-section view shown in FIG. 10B). Although not shown, tip 828 may include an insulating layer forming an exterior of tip 828, as discussed above.

Electrode 826 may be formed through an extrusion process. In this aspect, the electrode may be formed by pushing hot metal through an extrusion die to form shaft 830. The electrode may then be pressed or butted against the die such that a portion of the extrusion is forced outward to form a widened portion, for example, tip 828. Additionally, although not shown, electrode 826 may include an insulating layer, for example, on the outer surface of tip 828.

Figures 11A, 11B, 12A, 12B:
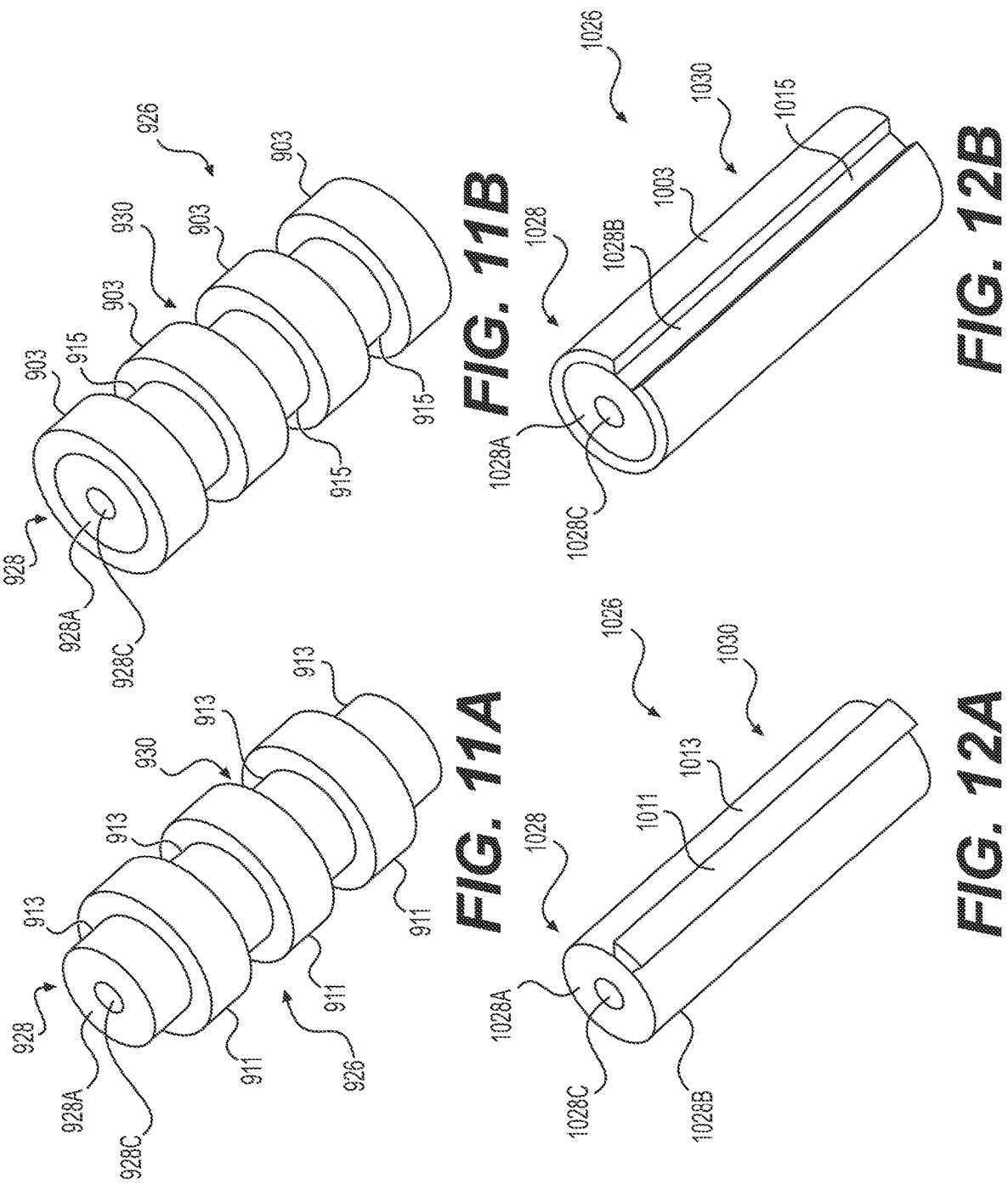
FIGS. 11A and 11B illustrate perspective views of another exemplary electrode portion of the medical device of FIGS. 1A and 1B, according to aspects of the disclosure.
FIGS. 12A and 12B illustrate perspective views of another exemplary electrode portion of the medical device of FIGS. 1A and 1B, according to aspects of the disclosure.

FIGS. 11A and 11B illustrate another alternative electrode 926 similar to electrode 26, with similar elements shown by 900 added to the reference numbers. FIG. 11A shows electrode 926 at an intermediate manufacturing step, and FIG. 11B shows a finished electrode 926. Electrode 926 includes tip 928 and an electrode shaft 930. Electrode shaft 930 may be substantially cylindrical and/or may include one or more contours discussed above. Electrode 926 includes a fluid delivery channel formed by an electrode shaft lumen (not shown) and a tip lumen 928C. Tip 928 includes a distal end 928A, and as shown in FIG. 11B, an insulated portion 903 may cover at least a portion of a side portion of tip 928. For example, insulated portion 903 may include a plurality of layers of insulation deposited on at least a portion of tip 928, as discussed above. Alternatively or additionally, an insulated tip (e.g., with a shape discussed herein) may be coupled to distal end 928A.

In one aspect, as shown in FIG. 11A, electrode 926 may be formed as a unitary piece of material, as discussed above. One or more masks 911 may be positioned on and/or around electrode 926 at various locations. Then, electrode 926, with mask(s) 911 on and/or around electrode 926, may be exposed to a deposition process, for example, a sputtering process, to deposit one or more insulating materials on exposed portions 913. The insulating materials may form a uniform, impermeable, insulating film or layers. In one aspect, the insulating materials may include a permeable film that includes dimensions small enough to prevent fluid, and thus electric charge, from percolating or otherwise passing through the insulating materials. The insulating material(s) may be deposited in one or more layers, and the insulating material may match or substantially match the thermal coefficients of expansion and/or the heat capacities of electrode 926 and/or the insulated tip that may be coupled to electrode 926. The insulating material(s) may be one or more of a metal, a metal alloy, metal oxide ($Al_2O_3$, a glass, etc.), etc., and may be chosen to help reduce or minimize thermal stresses between electrode 926 and the insulating material(s). Furthermore, a thickness of the insulating materials (films, layers, etc.) may depend on a dielectric strength and/or other characteristics of the insulating materials.

Mask(s) 911 may help prevent the insulating material from being deposited on the portion(s) of electrode 926 covered by mask(s) 911. Mask(s) 911 may be annular or ring-shaped portions that cover portions of electrode 926. For example, mask(s) 911 may be formed of an organic material, such as, for example, a polyimide, or an inorganic material, such as, for example, a ceramic, a metal, etc. The material that forms mask(s) 911 may depend on the coating process. Mask(s) 911 may be coupled to electrode 926 via one or more methods. For example, mask(s) 911 may be coupled to electrode 926 via a mechanical fixture in intimate contact, a plated metal that is subsequently removed by etching, a photo-resist coating (e.g., coating via a liquid of film), an adhesive (e.g., adhesive tape), dip coating, physical vapor deposition coating, chemical vapor deposition coating (or parylene coating), etc. Alternatively or additionally, mask(s) 911 may be coupled to the entirety of electrode 926, and portions may be removed where not desired, for example, by laser etching, chemical etching, machining, grinding, etc. After the deposition process, mask(s) 911 may be removed, forming electrode 926 with insulating portions 903 (from depositing insulative material) and uninsulated portions 915 (from portions that were masked). Insulating portions 903 may be annular or ring-shaped portions that cover portions of electrode 926 that were not masked. Uninsulated portions 915 may be annular or ring-shaped portions of electrode 926 that were masked. Mask(s) 911 may be longitudinally spaced apart along a length of electrode 926, for example, along a length of electrode shaft 930. Accordingly, insulating portions 903 and uninsulated portions 915 may be longitudinally spaced apart on a length of electrode shaft 930. For example, adjacent uninsulated portions 915 may be separated by insulating portions 903. Although not shown, mask(s) 911 may be any appropriate shape and/or spacing in order to form electrode 926 with an appropriate shape and/or spacing of insulating portions 903 and uninsulated portion 915. It is noted that, although not shown, distal end 928A and/or tip lumen 928C may be masked or otherwise covered to help prevent insulating layers 903 from blocking tip lumen 928C.

As shown in FIG. 11B, insulating layer 903 may be deposited on one or more portions of electrode 926, in addition to tip 928. In this aspect, reducing the uninsulated portions 915 of electrode 926 may help to control and/or reduce a thermal build-up on and/or around electrode 926, which may help a user perform controlled cuts and/or otherwise treat tissue.

FIGS. 12A and 12B illustrate another alternative electrode 1026 similar to electrode 26, with similar elements shown by 1000 added to the reference numbers. FIG. 12A shows electrode 1026 at an intermediate manufacturing step, and FIG. 11B shows a finished electrode 1026. Electrode 1026 includes a tip 1028 and an electrode shaft 1030. Electrode shaft 1030 may be substantially cylindrical and/or may include one or more contours discussed above. Electrode 1026 includes a fluid delivery channel formed by an electrode shaft lumen (not shown) and a tip lumen 1028C. Tip 1028 includes a distal end 1028A and a side portion 1028B, and an insulated portion 1003 may cover at least a portion of side portion 1028B of tip 1028. For example, insulated portion 1003 may be deposited on at least a portion of tip 1028, as discussed above. Alternatively or additionally, an insulated tip (e.g., with a shape discussed herein) may be coupled to distal end 1028A.

In one aspect, as shown in FIG. 12A, electrode 1026 may be formed as a unitary piece of material, as discussed above. One or more masks 1011 may be positioned on and/or around electrode 1026 at one or more locations, and mask(s) 1011 may help prevent the insulating material from being deposited on the portion(s) of electrode 1026 covered by mask(s) 1011.

As shown in FIG. 12A, one mask 1011 may extend longitudinally and span a circumferential portion of the exterior of electrode 1026. For example, mask 1011 may span approximately 15-90 degrees of a circumferential exterior of electrode 1026, for example, of electrode shaft 1030. In another aspect, mask 1011 may span up to approximately 180 degrees of the circumferential exterior of electrode 1026. As such, when electrode 1026 is exposed to the deposition process, an insulated portion 1003 may be formed, for example, by depositing one or more insulating layers on the portion of electrode 1026 not covered by mask 1011, for example, exposed portion 1013, which may span approximately 180 to 345 degrees about a circumference of electrode 1026. In this aspect, insulated portion 1003 may form a circumferential insulation and one or more uninsulated portions 1015. Uninsulated portion(s) 1015 may span an entire length of electrode 1026, or may span only a portion of the length of electrode 1026. Moreover, the size and/or width of mask 1011 may vary along the length of electrode 1026 to form uninsulated portion(s) 1015 with a varied width, as measured about the circumference. In these aspects, a user may use electrode 1026 and uninsulated portion(s) 1015 to perform controlled cuts and/or otherwise treat tissue.

Figures 13, 14A, 14B:
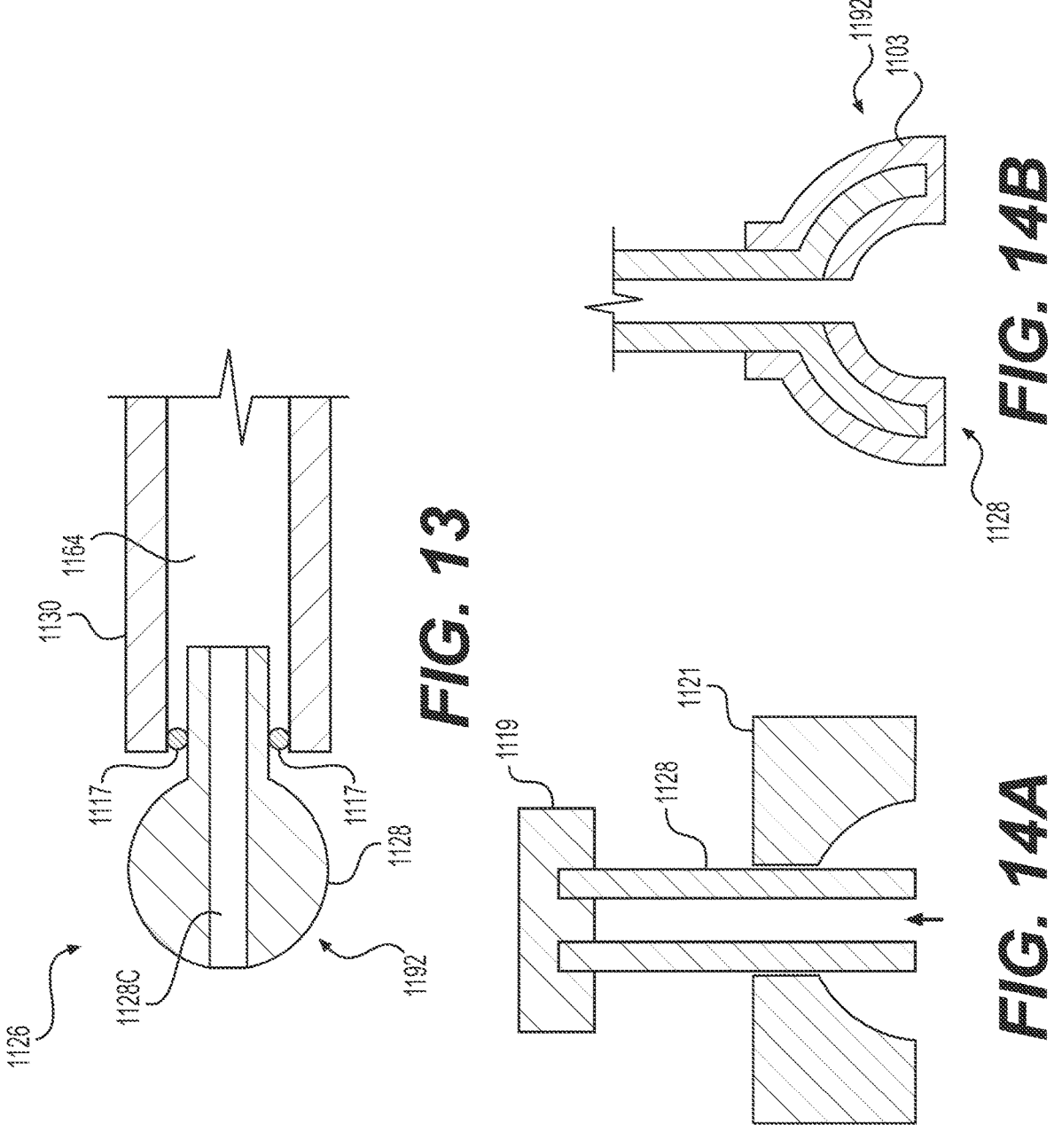
FIG. 13 illustrates a cross-sectional view of another exemplary electrode portion of the medical device of FIGS. 1A and 1B, according to aspects of the disclosure.
FIGS. 14A and 14B illustrate cross-sectional views of a formation process that may be performed to form the electrode portion of the medical device of FIGS. 1A and 1B, according to aspects of the disclosure.

FIG. 13 illustrates a partial cross-sectional view of another alternative electrode 1126 similar to electrode 26, with similar elements shown by 1100 added to the reference numbers. Electrode 1126 includes tip 1128 and an electrode shaft 1130. Electrode shaft 1130 includes an electrode shaft lumen 1164. Electrode shaft 1130 may be a catheter, for example, a hypotube, which may be formed of an appropriate material, for example, stainless steel. As shown, tip 1128 may be secured within shaft 1130, for example, via a circumferential laser weld 1117 or another appropriate coupling mechanism. For example, a proximal portion of tip 1128 may include a reduce diameter or width, and the proximal portion of tip 1128 may be positioned within shaft 1130. Tip 1128 may be formed of a machined metal, and may include a tip lumen 1128C fluidly connected to electrode shaft lumen 1164, as discussed above.

As discussed below with respect to FIGS. 14A, 14B, 15A, 15B, 16A, and 16B, tip 1128 may be formed to include a widened end portion 1192. Widened end portion 1192 may include a round or bulbous distal portion. Widened end portion 1192 may include a cross-sectional diameter or width that is larger than the cross-sectional diameter or width of electrode shaft lumen 1164. At least a portion of tip 1128 may be coated in an insulating material, as discussed above.

FIGS. 14A and 14B illustrate one method to form a widened end portion 1192 of an electrode tip. For example, FIG. 14A illustrates a cross-sectional view of tip 1128 without widened end portion 1192, and FIG. 14B illustrates a cross-sectional view of tip 1128 with widened end portion 1192. One end of tip 1128 may be coupled to a plug 1119, and another end of tip 1128 may be positioned within a die 1121. Die 1121 may include an inner shape that corresponds to a desired shape of widened end portion 1192. In one aspect, mechanical pressure may be applied to push the portion of tip 1128 to take the shape of die 1121. For example, an incompressible material (e.g., a rubber or other material, for example, with a Poisson's ratio of approximately 0.5), a sacrificial compressible material, or a forming tool may be inserted into the portion of tip 1128 within die 1121. As a result, the portion of tip 1128 within die 1121 may expand radially outwardly to take the shape of die 1121, as shown in FIG. 14B. In another aspect, a pressurized fluid may delivered through tip 1128, for example, as indicated by the arrow in FIG. 14A, such that the pressure from the fluid pushes a portion of tip 1128 radially outwardly to take the shape of die 1121, as shown in FIG. 14B. Accordingly, the portion of tip 1128 within die 1121 may form widened end portion 1192. Widened end portion 1192 may be semicircular, hemispherical, etc. It is noted, however, that the resulting shape of widened end portion 1192 depends on the shape of die 1121. As discussed above, an insulating layer 1103 may be deposited on a portion of tip 1128, for example, on at least widened end portion 1192. Insulating layer 1103 may also be deposited on an inner face of widened end portion 1192, as shown in FIG. 14B.

Figure 15A:
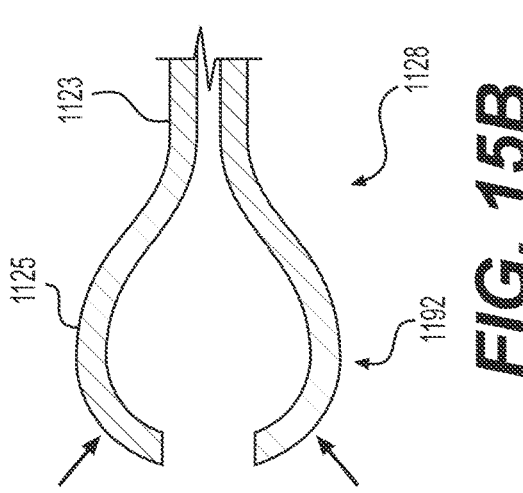
FIGS. 15A and 15B illustrate cross-sectional views of a formation process that may be performed to form the electrode portion of the medical device of FIGS. 1A and 1B, according to aspects of the disclosure.
Figure 15B:
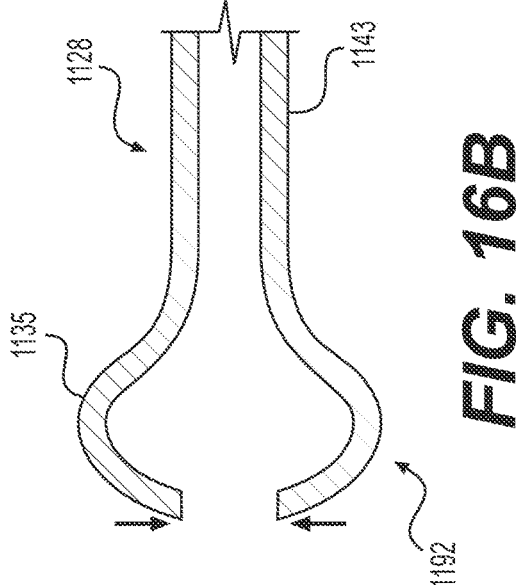

FIGS. 15A and 15B illustrate another method to form widened end portion 1192. For example, FIG. 15A illustrates a cross-sectional view of tip 1128 without widened end portion 1192, and FIG. 15B illustrates a cross-sectional view of tip 1128 with widened end portion 1192. As shown in FIG. 15A, tip 1128 may be swaged or otherwise compressed to form a narrow portion 1123, as shown by the arrows in FIG. 15A, leaving a wide portion 1125. Then, as shown in FIG. 15B, force may be applied to wide portion 1125, for example, at an end of wide portion 1125 as shown by the arrows in FIG. 15B, to form widened end portion 1192, which may be rounded. However, it is noted that the applied forces leave an opening at the distalmost end of widened end portion 1192, for example, to allow for fluid delivery. As discussed above, an insulating layer (not shown) may be deposited on a portion of tip 1128, for example, on at least widened end portion 1192.

Figure 16A:
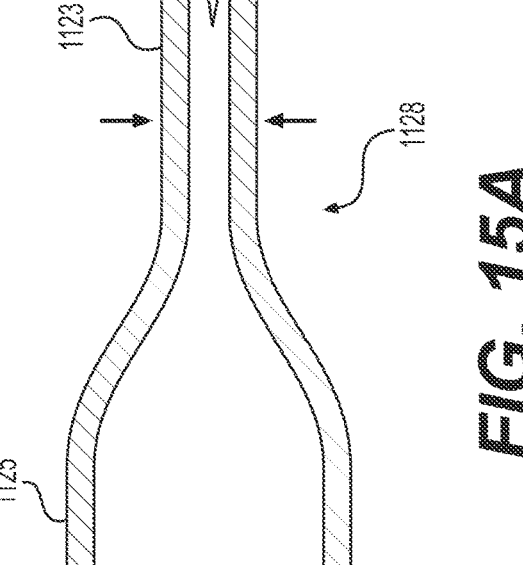
FIGS. 16A and 16B illustrate cross-sectional views of a formation process that may be performed to form the electrode portion of the medical device of FIGS. 1A and 1B, according to aspects of the disclosure.
Figure 16B:
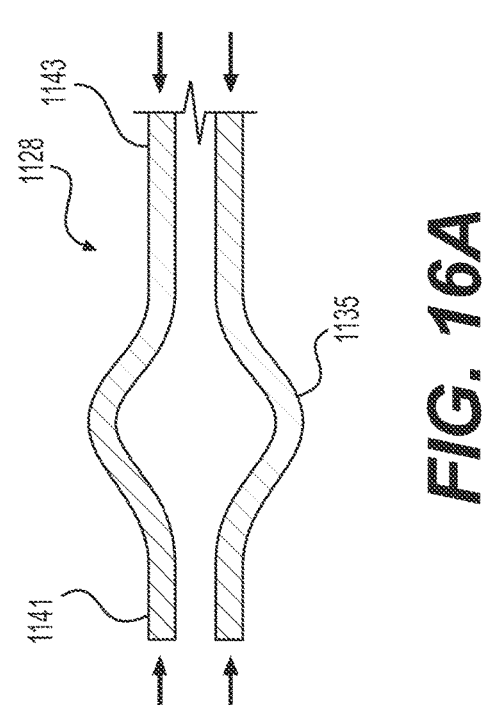

FIGS. 16A and 16B illustrate another method to form widened end portion 1192. For example, FIG. 16A illustrates a cross-sectional view of tip 1128 without widened end portion 1192, and FIG. 16B illustrates a cross-sectional view of tip 1128 with widened end portion 1192. As shown in FIG. 16A, tip 1128 may be compressed, for example, longitudinally as shown by the arrows in FIG. 16A, to form a bulge 1135, which is wider than narrow end portions 1141, 1143. Then, as shown in FIG. 16B, force, for example, a cutting force, as shown by the arrows in FIG. 16B, may be applied to an end of bulge 1135 (e.g., an interface or transition portion between bulge 1135 and end portion 1141) to form widened end portion 1192, which may be rounded. In one aspect, the cutting force may cut end portion 1141 from bulge 1135, and the cutting force may also bend and/or shape electrode 1128 to include widened end portion 1192. Alternatively, the cutting force may cut end portion 1141 from bulge 1135, and then an additional force may be applied to bulge 1135 to bend and/or shape electrode 1128 to include widened end portion 1192. Nevertheless, as mentioned with respect to FIGS. 15A and 15B, the applied forces leave an opening at the distalmost end of widened end portion 1192, for example, to allow for fluid delivery. As discussed above, an insulating layer (not shown) may be deposited on a portion of tip 1128, for example, on at least widened end portion 1192.

The aspects mentioned above may allow for electrode 1126 to include a flared or widened end portion 1192 without separate additive or subtractive processes. The flared or widened end portion 1192 shown in FIGS. 13-16B, and discussed throughout this disclosure, may help a user separate tissue or other material from a cutting surface of electrode 1126, which may help to prevent or minimize damage and/or unintended contact between electrode 1126 and the tissue. Moreover, the above formation methods may be varied to form widened end portions 1192 of varying sizes, shapes, etc.

While above aspects, including FIGS. 13-16B, discuss tip 1128 and electrode shaft 1130 being separate components, it is contemplated that tip 1128 and electrode shaft 1130 may be integrally formed. For example, a single piece of material (e.g., a hypotube) may be formed to have a shape corresponding to electrode 1126, and only a portion of electrode 1126, for example, tip 1128, may be insulated with an insulating material. Moreover, widened end portion 1192 of tip 1128 may be formed by depositing the insulating material on tip 1128. In another aspect, widened end portion 1192 of tip 1128 may be formed by adding material (e.g., soldering, machining, etc.) to tip 1128.

It is noted that different electrodes may treat and/or manipulate tissue differently (e.g., based on the size and/or shape of the electrodes). For example, different electrodes may be coupled to distal end 16 for different procedures. In one aspect, a first electrode, for example, electrode 326 may be useful for a first type of procedure, and a second electrode, for example, electrode 426 may be useful for a second type of procedure. Similarly, a third electrode, for example, electrode 526 may be useful for a third type of procedure. Nevertheless, as discussed above with respect to electrode 26, the electrodes discussed herein may be used to treat or manipulate tissue (e.g., by delivering energy via the electrode shaft) and deliver fluid distally from the distal end, with the distal end of the electrode insulated.

The electrodes, including the insulation tips (or tips with insulating layer forming the exterior of the tips) and electrode shafts, help to provide a standoff or insulation between a distal portion of the electrode and tissue at the target site.

Additionally, the various electrodes may help to allow for a device that may be used to both cut, dissect, ablate, mark, or otherwise treat tissue, and also deliver fluid to the target site. The fluid may be delivered to the target site distally out of the distal end of the electrode. Additionally, in at least some aspects, the fluid being delivered to the target site may be non-conductive.

The various electrodes discussed herein are capable of modifying physical properties of tissue when in contact with tissue by delivering energy (e.g., radio frequency energy). The energy delivered may be monopolar or bipolar energy. The various electrodes may be coupled to a shaft, with the shaft configured to extend into a body lumen or cavity of a subject. The shaft includes an electrical element traversing the shaft and connecting the electrode to an energy source, for example, in the handle or coupled to the handle.

As discussed, the electrodes may also be coupled to an actuation member (e.g., movable body 20), for example, in the handle or coupled to the handle, that allows a user to translate the electrode relative to the shaft. The electrode may be translatable between at least a first position in which a cutting shaft (e.g., longitudinal portion 62), of the electrode is retracted within the shaft, and a second position in which the cutting shaft is extended beyond the shaft and exposed. In both the first and second positions, the distal portion that includes the insulated portions (e.g., insulation tip 28 or tips with insulating layers forming the exterior layer of the tips) may be extended and exposed beyond the shaft, and not retracted within the shaft. Moreover, the handle may allow for the electrodes to be positioned in one or more intermediate position (i.e., a position in which only a portion of longitudinal portion 62 is exposed).

As such, the insulated distal end face (e.g., insulation tip 28 or tips with insulating layers forming the exterior layer of the tips) may abut tissue and help to prevent or minimize damage or unintended contact of the electrode with the tissue. The user may also position the uninsulated electrode shaft to abut or contact tissue and apply energy to cut, dissect, ablate, mark, or otherwise treat tissue. The insulation tips may be coupled to the electrode shaft in various ways, which may allow for the insulation tip to be coupled to an existing uninsulated electrode shaft and then used in a procedure.

In one example, an electrosurgical generator coupled to the handle (or within the handle) may generate receive energy in various modes, for example, radio frequency energy in a cutting mode, a coagulation mode, etc., in order for the electrode to deliver these different modes of energy to the tissue. In one aspect, the electrosurgical generator and/or the handle may include one or more knobs, dials, buttons, etc. in order to select the energy mode. Additionally, in one example, a fluid source (e.g., a saline source) coupled to the handle may provide fluid (e.g., saline) to be delivered through the electrode to the tissue and/or the target site. The fluid may be delivered at a constant rate, a pulsed rate, a user-controlled rate, etc. In these aspects, one or more of the energy delivery and/or the fluid delivery may be controlled by one or more actuators (e.g., triggers, buttons, touch screens, foot pedals, etc.).

The medical devices and methods discussed above allow a user to treat tissue by delivering electrical energy into the tissue, and delivering fluid, either simultaneously or sequentially. For example, a user may couple an electrode to the distal end and deliver the distal end to an interior lumen of a subject to deliver medical therapy in a portion of a procedure (e.g., mark, cauterize, or resect tissue). The insulation tip (or insulating layer forming the exterior of a tip)

may help to prevent or minimize damage and/or unintended contact between the electrode and the tissue. The user may also deliver fluid distally out of the distal end of the electrode, either simultaneously or sequentially with the energy delivered, which may help the user to more quickly and efficiently deliver the medical therapy, for example, cut, dissect, ablate, mark, coagulate, cauterize, or otherwise treat tissue. Moreover, the user may deliver fluid and energy without removing the medical device from the patient or subject, which may help to reduce the costs and duration of the procedure, also potentially reducing the risks to the subject.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
a shaft including a shaft lumen configured to direct a flow of fluid through the shaft;
an electrode shaft configured to deliver energy to a target site and including:
an electrode shaft lumen configured to deliver fluid from the shaft lumen to the target site; and
a distal end including a widened portion that extends radially outward relative to a longitudinal axis of the electrode shaft; and
a tip coupled to the distal end of the electrode shaft, the tip including:
two half portions that each include at least one groove on a radially inner face,
wherein each groove is configured to receive at least a portion of the widened portion of the distal end of the electrode shaft,
wherein each groove extends radially outward relative to the longitudinal axis of the electrode shaft, and
wherein each half portion includes at least an exterior layer of insulative material; and
an electrode plate on a proximal end of the tip, wherein the electrode plate is a separate component from the electrode shaft and the tip, and wherein the electrode plate is coupled to the proximal end of the tip,
wherein the insulative material of the tip encapsulates an entire distal end of conductive material of the distal end of the electrode shaft,
wherein the tip includes a tip lumen fluidly connected to the electrode shaft lumen and configured to deliver fluid to the target site, wherein the tip lumen and the electrode shaft lumen are longitudinally aligned and fluidically connected, and wherein a distal end portion of the tip lumen includes a widened chamfer to disperse fluid delivered to a target site, and
wherein the electrode shaft and the tip with the exterior layer of insulative material are longitudinally movable together relative a distal end of the shaft.

2. The medical device of claim 1, wherein the tip lumen is positioned entirely distal from the electrode shaft lumen.

3. The medical device of claim 2, wherein an entire exterior of the tip comprises the exterior layer, and wherein the exterior layer is formed by a sputtering procedure.

4. The medical device of claim 3, wherein the insulative material is ceramic.

5. The medical device of claim 4, wherein the exterior layer is approximately 300 microns thick.

6. The medical device of claim 1, wherein the tip includes a rounded distal end and a cylindrical side portion.

7. The medical device of claim 1, wherein the tip is cylindrical and includes rounded edges.

8. The medical device of claim 1, wherein the electrode shaft includes a plurality of insulated portions, and wherein the plurality of insulated portions are longitudinally spaced apart on a length of the electrode shaft.

9. The medical device of claim 1, wherein the electrode plate is conductive and is electrically connected to the electrode shaft such that the electrode plate is energized when the electrode shaft is energized.

10. The medical device of claim 9, wherein the electrode plate is circular and covers an entirety of the proximal end of the tip.

11. The medical device of claim 9, wherein the electrode plate is triangular or star shaped.

12. The medical device of claim 1, wherein the electrode shaft is formed of one piece of metallic material.

13. A medical device, comprising:
a handle including a fluid port and an energy receiving hub;
a shaft including a shaft lumen configured to direct a flow of fluid through the shaft from the fluid port;
a conductive element electrically connected to the energy receiving hub and passing through at least a portion of the handle and/or the shaft; and
an electrode coupled to a distal end of the shaft, wherein the electrode includes an electrode shaft and a tip extending distally from and fixedly coupled to the electrode shaft, and wherein the tip includes an inner portion of conductive material and an exterior layer of an insulative material,
wherein the insulative material encapsulates an entire distal end of the conductive material,
wherein the electrode shaft is electrically connected to the conductive element and includes an electrode shaft lumen fluidly connected to the shaft lumen, and
wherein the tip includes a tip lumen extending through the exterior layer of insulative material, and wherein the tip lumen is fluidly connected to the electrode shaft lumen and configured to deliver fluid from a distal end of the electrode;
wherein the electrode shaft and the tip are extendable and retractable together relative to the shaft;
wherein the insulative material includes (i) a first half portion including a first portion of the tip lumen, and (ii) a second half portion including a second portion of the tip lumen, and wherein the first half portion and the second half portion are separate components that are coupled together to encapsulate the entire distal end of the conductive material and to form the tip lumen; and
wherein the distal end of the electrode shaft or the conductive material of the tip includes a widened end portion, wherein the widened end portion extends radially outward relative to a longitudinal axis of the electrode shaft, wherein the first half portion and the second half portion of the tip each includes a groove on a radially inner face, wherein each groove is configured to receive at least a portion of the widened end portion, and wherein each groove extends radially outward relative to the longitudinal axis of the electrode shaft.

14. The medical device of claim 13, wherein the handle further includes a main body and a movable body, wherein movement of the movable body relative to the main body moves the electrode, including the electrode shaft and the tip, relative to the distal end of the shaft.

15. The medical device of claim 14, wherein, with the movable body in a proximally retracted position, only the tip of the electrode is exposed distally beyond the shaft, wherein, with the movable body in a distally extended position, the tip of the electrode and at least a portion of the electrode shaft are exposed distally beyond the shaft, and wherein a distal end portion of the tip lumen includes a widened chamfer to disperse fluid delivered to a target site.

16. A medical device, comprising:

an electrode shaft including an electrode shaft lumen configured to receive fluid, wherein a distal end of the electrode shaft includes a widened end portion, wherein the widened end portion extends radially outward relative to a longitudinal axis of the electrode shaft; and a tip fixedly coupled to a distal tip of the electrode shaft and including insulative material, wherein the insulative material of the tip includes a first tip half portion and a second tip half portion, and wherein the first tip half portion is a separate component from the second tip half portion, and wherein the first tip half portion is welded to the second tip half portion with the electrode shaft positioned between the first tip half portion and the second tip half portion, wherein the insulative material insulates at least a distal portion of the medical device, including insulating at least an entirety of the distal tip of the electrode shaft, wherein the tip includes a tip lumen fluidly connected to the electrode shaft lumen to form a channel, wherein the tip lumen extends through insulative material formed by the first tip half portion and the second tip half portion, and wherein a distal end portion of the tip lumen includes a widened chamfer to disperse fluid delivered to a target site, wherein the channel extends through the electrode shaft and the tip along a longitudinal axis of the medical device, and wherein the insulative material of the tip includes a groove on a radially inner face in each of the first tip half portion and the second tip half portion, wherein each groove extends radially outward relative to the longitudinal axis of the electrode shaft, and wherein each groove is configured to receive a portion of the widened end portion when the first tip half portion of insulative material and the second tip half portion of insulative material are welded together.

17. The medical device of claim 16, wherein the tip formed by the first tip half portion and the second tip half portion includes a rounded distal portion and a cylindrical side portion.

18. The medical device of claim 16, wherein the insulative material is ceramic.

19. The medical device of claim 13, wherein each of the first tip half portion and the second tip half portion include a partially cylindrical side portion and a partially rounded distal portion.

\* \* \* \* \*